(12) United States Patent
Zagorchev et al.

(10) Patent No.: US 12,102,489 B2
(45) Date of Patent: Oct. 1, 2024

(54) IMAGE-GUIDED SURGICAL SYSTEMS WITH QUANTITATIVE EVALUATION OF IN VIVO THERMAL TREATMENTS AND RELATED METHODS

(71) Applicant: ClearPoint Neuro, Inc., Solana Beach, CA (US)

(72) Inventors: Lyubomir Georgiev Zagorchev, Burlington, MA (US); Christian Richard Osswald, Elk Grove Village, IL (US); Nicolas Gallo, Newport Beach, CA (US); Kamal Vij, Chandler, AZ (US)

(73) Assignee: ClearPoint Neuro, Inc., Solana Beach, CA (US)

(*) Notice: Subject to any disclaimer, the term of this patent is extended or adjusted under 35 U.S.C. 154(b) by 252 days.

(21) Appl. No.: 17/725,077

(22) Filed: Apr. 20, 2022

(65) Prior Publication Data

US 2023/0000561 A1 Jan. 5, 2023

Related U.S. Application Data

(60) Provisional application No. 63/216,738, filed on Jun. 30, 2021.

(51) Int. Cl.
*A61B 5/00* (2006.01)
*A61B 5/01* (2006.01)
(Continued)

(52) U.S. Cl.
CPC ............ *A61B 90/37* (2016.02); *A61B 5/0036* (2018.08); *A61B 5/0042* (2013.01); *A61B 5/015* (2013.01);
(Continued)

(58) Field of Classification Search
CPC ..... A61B 90/37; A61B 5/0036; A61B 5/0042; A61B 5/015; A61B 5/7425; A61B 18/20;
(Continued)

(56) References Cited

U.S. PATENT DOCUMENTS 6,050,992 A 4/2000 Nichols
6,167,311 A 12/2000 Rezai
(Continued)

FOREIGN PATENT DOCUMENTS

EP 2055232 A2 5/2009
WO 2009124301 A1 10/2009

OTHER PUBLICATIONS

"NeuroQuant" From URL: https://www.cortechslabs.com/products/neuroquant/ (10 pages) Accessed on: Apr. 30, 2020.
(Continued)

*Primary Examiner* — Alexei Bykhovski
(74) *Attorney, Agent, or Firm* — Myers Bigel, P.A.

(57) ABSTRACT

Methods and systems that provide quantitative assessments of in vivo thermal treatments, such as ablations, during image-guided surgeries using a high-resolution pre-operative MRI image segmented with a shape constrained and deformable mesh representations of brain structures and generating 3-D visualizations of thermally treated volumes during the thermal treatment that can provide near real time visual and quantitative feedback to a clinician.

26 Claims, 14 Drawing Sheets

(51) Int. Cl.

| | | |
|---|---|---|
| *A61B 18/20* | (2006.01) | |
| *A61B 34/00* | (2016.01) | |
| *A61B 34/10* | (2016.01) | |
| *A61B 90/00* | (2016.01) | |
| *A61B 90/10* | (2016.01) | |
| *G06T 7/11* | (2017.01) | |
| *A61B 5/055* | (2006.01) | |
| *A61B 18/00* | (2006.01) | |

(52) U.S. Cl.
CPC ............ *A61B 5/7425* (2013.01); *A61B 18/20* (2013.01); *A61B 34/10* (2016.02); *A61B 34/25* (2016.02); *A61B 90/10* (2016.02); *G06T 7/11* (2017.01); *A61B 5/055* (2013.01); *A61B 2018/00446* (2013.01); *A61B 2090/374* (2016.02)

(58) Field of Classification Search
CPC ......... A61B 34/10; A61B 34/25; A61B 90/10; A61B 5/055; A61B 2018/00446; A61B 2090/374; A61B 2018/00321; A61B 2018/00577; A61B 2018/00809; A61B 2018/2005; A61B 2090/365; A61B 2090/3937; A61B 2034/105; A61B 2034/107; A61B 90/11; G06T 7/11
See application file for complete search history.

(56) References Cited

U.S. PATENT DOCUMENTS

| | | |
|---|---|---|
| 6,356,786 B1 | 3/2002 | Rezai et al. |
| 6,405,079 B1 | 6/2002 | Ansarinia |
| 6,438,423 B1 | 8/2002 | Rezai et al. |
| 6,526,318 B1 | 2/2003 | Ansarinia |
| 6,539,263 B1 | 3/2003 | Schiff et al. |
| 6,609,030 B1 | 8/2003 | Rezai et al. |
| 6,708,064 B2 | 3/2004 | Rezai |
| 8,195,272 B2 | 6/2012 | Piferi et al. |
| 8,315,689 B2 | 11/2012 | Jenkins et al. |
| 8,369,930 B2 | 2/2013 | Jenkins et al. |
| 10,905,498 B2 | 2/2021 | Birenbaum et al. |
| 2009/0221999 A1 | 9/2009 | Shahidi |
| 2010/0312094 A1 | 12/2010 | Guttman et al. |
| 2015/0209551 A1* | 7/2015 | Burdette ........... A61M 25/0127 600/411 |
| 2015/0257830 A1 | 9/2015 | Tyc et al. |
| 2017/0065349 A1* | 3/2017 | Ourselin ................ A61B 34/10 |
| 2019/0347795 A1* | 11/2019 | Zagorchev ............. G16H 30/40 |
| 2021/0264623 A1* | 8/2021 | Tandon ................ A61B 5/7425 |
| 2021/0282866 A1 | 9/2021 | Vij et al. |
| 2021/0343397 A1 | 11/2021 | Orr et al. |

OTHER PUBLICATIONS

"WayPoint™ Navigator Software" From URL: https://www.fh-co.com/product/waypoint-navigator-software (4 pages) Accessed on: Apr. 30, 2020.

Tani et al. "Three-dimensional quantitative assessment of ablation margins based on registration of pre- and post-procedural MRI and distance map" International Journal of Computer Assisted Radiology and Surgery, 11 (6):1133-1142 (2016).

Weese et al. "Shape-Constrained Deformable Models and Applications in Medical Imaging" Shape Analysis in Medical Image Analysis, Lecture Notes in Computational Vision and Biomechanics 14:151-184 (2014).

Aansneurosurgery: "Laser interstitial thermal therapy for an eloquent region supratentorial brain lesion" retrieved from Internet Jul. 25, 2022, URL: https://www.youtube.com/watch?v=ndrTgi6MXqE (see timestamps 0:33, 1:50, 2:05, 4:54, 5:00, 5:18, 5:42).

Brainlab "iPlan FiberTracking" retrieved from internet Jul. 26, 2022, URL: https://www.brainlab.com/wp-content/uploads/2014/01/White-Paper-Fiber-Tracking-Technology.pdf (pp. 1-2) (Aug. 2012).

International Search Report and the Written Opinion of the International Searching Authority corresponding to International Patent Application No. PCT/US2022/025564 (19 pages) (mailed Aug. 3, 2022).

* cited by examiner

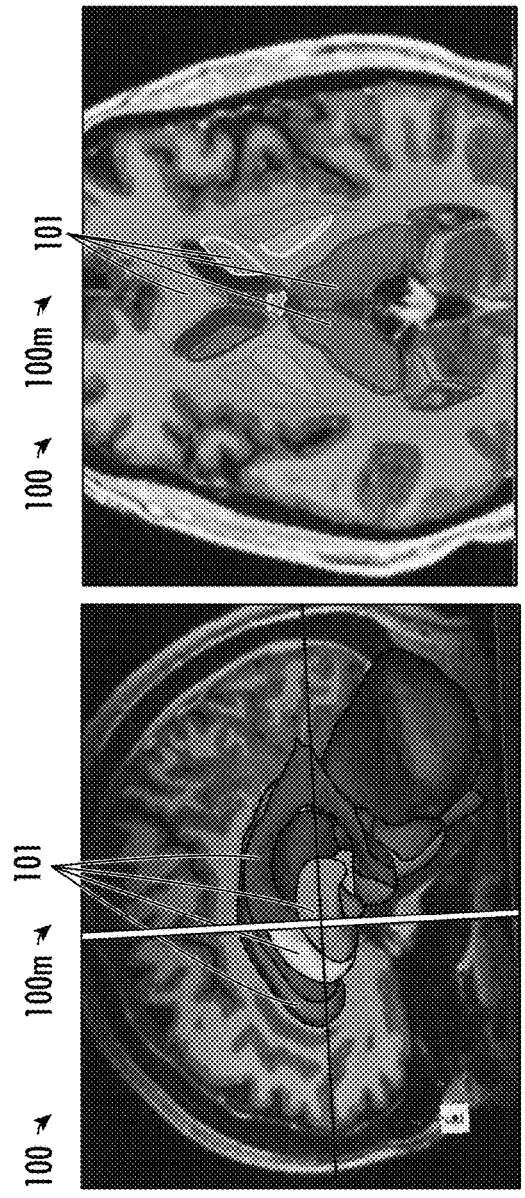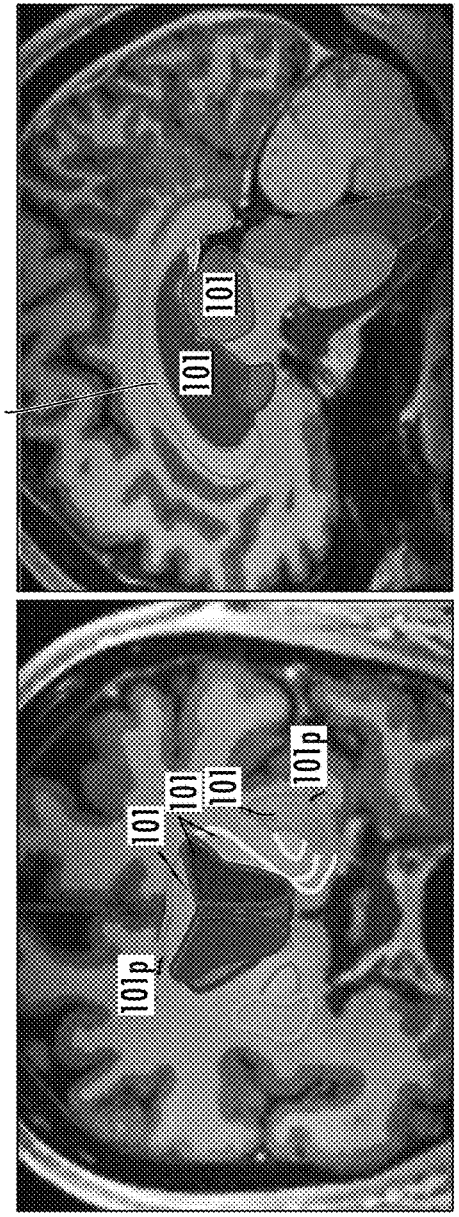
FIG. 1A  FIG. 1B  FIG. 1C  FIG. 1D

100m

100m

IMAGE-GUIDED SURGICAL SYSTEMS WITH QUANTITATIVE EVALUATION OF IN VIVO THERMAL TREATMENTS AND RELATED METHODS

RELATED APPLICATIONS

This application claims the benefit of and priority to U.S. Provisional Application Ser. No. 63/216,738, filed Jun. 30, 2021, the contents of which are hereby incorporated by reference as if recited in full herein.

FIELD OF THE INVENTION

The present invention relates to image-guided surgical systems.

BACKGROUND

Laser Interstitial Thermal Therapy (LITT) is a promising new procedure used to perform minimally invasive ablations in the brain. LITT uses collimated light with a diffusing tip to deliver heat to cells. Blood vessels dilate with temperatures of up to 40° C., which result in an increased blood flow. Temperatures in the range of 40° C. to 60° C. cause denaturation of DNA and irreversible cell damage. Temperatures above 60° C. cause/induce substantially instant cell death. Temperatures greater than 100° C. vaporize water and cause carbonization of surrounding tissue. Magnetic Resonance Imaging (MRI) is used to create thermal images of the ablated tissue and to monitor the laser-tissue interaction during the LITT procedure. Known clinical centers perform additional structural MRI at the end of a LITT procedure to visually verify the amount of ablated tissue. However, post-operative qualitative data may under or overestimate the actual ablation due to changes in local tissue contrast.

Conventional clinical workflow may not detect and/or may not accurately be able to monitor the actual effect of ablation on target regions and surrounding healthy brain tissue. Accurate monitoring/determination of ablated volume as well as functional integrity/connectivity of ablated regions can be important for the efficacy of LITT and may be able to provide better patient outcomes.

SUMMARY

Embodiments of the present invention are directed to systems, methods and computer program products configured to provide quantitative evaluation of thermally treated tissue during image-guided thermal surgical procedures such as during LITT procedures.

Embodiments of the present invention can provide systems, methods and computer program products that can improve thermal procedures such as ablation and/or LITT procedures to avoid non-target brain tissue damage, risk of complications, and/or reduce or avoid unintended neurologic deficits.

Embodiments of the present invention provide methods, systems and computer program products that can facilitate reproducible thermal therapies of the brain (optionally ablations) to thereby facilitate therapies with the goal of improved, if not optimal, functional/neurological outcome.

Embodiments of the present invention can improve the efficacy of LITT and may also eliminate the need for subsequent (repeat) visits/ablations.

Embodiments of the present invention employ patient-specific, shape-constrained segmentation of a brain of a patient and mesh geometry/models to brain structures to define safety points and/or zones to facilitate thermal evaluation of thermal exposure information inside and outside a target treatment region.

Embodiments of the present invention are directed to image-guided surgical systems. The systems include a workstation with a display and a computer system in communication with or at least partially onboard the workstation. The computer systems are configured to: provide a brain of a patient segmented to show patient-specific brain structures with three-dimensional mesh representations having surface conformable mesh elements that can be visualized three dimensions corresponding to three-dimensional MRI imaging space. Temperatures can be monitored in the target treatment region and in one or more safety zones adjacent the target treatment region in one or more volumes of tissue in near real-time during the thermal treatment.

The mesh representation can be a high-resolution mesh representation that is shape-constrained and can be surface conformable and/or comprise deformable mesh elements and adapt to geometry and topology of patient-specific structures of the brain and/or segments thereof of each respective patient.

The mesh representation can have a contiguous configuration of a plurality of triangular mesh elements.

Embodiments of the invention are directed to an image-guided surgical system. The system includes: a workstation with a display; and a computer system in communication with or at least partially onboard the workstation. The computer system is configured to provide visualizations of pre-operative high-resolution Magnetic Resonance Imaging (MRI) images of a brain of a patient to the display. The visualizations are segmented to show patient-specific brain structures with corresponding three-dimensional mesh representations, each mesh representation having surface conformable mesh elements that cover a respective patient-specific brain structure including a first mesh representation for a first patient-specific brain structure associated with a target thermal treatment region and a second mesh representation for a second patient-specific brain structure outside the target thermal treatment region. The computer system is also configured to define at least one safety zone using one or more mesh elements of the second mesh representation; monitor temperatures during an in vivo thermal treatment of the target thermal treatment region using MR images and the first and second mesh representations; and provide three-dimensional visualizations during the in vivo thermal treatment to the display that map temperatures to the first mesh representation and the second mesh representation.

The at least one safety zone can be identified and/or defined, at least in part, using vertex coordinates in MRI image space of at least one of the mesh elements of the second mesh representation and a distance of the at least one the mesh elements from either a neighboring segment of the first mesh representation or a distance to a trajectory line of a thermal treatment device providing the thermal treatment or distances from both the first mesh representation and the trajectory line.

The at least one safety zone can be identified and/or defined, at least in part, based on a location of at least one of the mesh elements or a vertex location of the at least one of the mesh elements corresponding to the mesh element that is closest to the first mesh representation and/or that is closest to a trajectory line of a thermal treatment device providing the thermal treatment.

The at least one safety zone can be identified and/or defined, at least in part, using a distance of a (virtual) line that is normal to a surface defined by one or more of the mesh elements.

The mesh elements can be triangular mesh elements, each having three vertices, optionally some of the mesh elements share one or more vertices.

The first and second mesh representations can each comprise a contiguous configuration of a plurality of triangular mesh elements, each triangular mesh element having a first vertex, a second vertex and a third vertex.

The computer system can be further configured to: obtain high-resolution MRI images during the in vivo thermal treatment; correlate and/or register the pre-operative high-resolution MRI images to the obtained high-resolution MRI images; and detect intensity changes in regions of interest in the first mesh representation and the second mesh representation relative to baseline values in the pre-operative high-resolution images in near real-time during the in vivo thermal treatment.

A defined temperature(s) can be encoded to mesh elements of at least the first mesh representation.

The defined temperature(s) can include at least one defined temperature, optionally a minimum treatment temperature, a maximum treatment temperature or both a minimum and a maximum treatment temperature at one or more mesh elements of the second mesh representation.

The computer system can be further configured to evaluate one or more of a center of mass, a principal axis and a mesh curvature of the first and/or second mesh representation and/or mesh elements thereof whereby one or more of the center of mass, principal axis, mesh curvature can be used to define trajectories for defining coverage for the thermal treatment.

The workstation can be in communication with an MRI scanner. The workstation can have a DICOM interface that receives images from the MRI scanner to provide image data during the thermal treatment.

The thermal treatment can be an ablation and the provided visualizations can be generated during the in vivo thermal treatment and show successively acquired images of volumes of ablated tissue and functional integrity/connectivity of ablated regions during the in vivo thermal treatment.

The thermal treatment can be a laser interstitial thermal therapy (LITT).

The pre-operative high-resolution MRI images can include T1W images.

Other embodiments are directed to methods of monitoring an in vivo thermal treatment of a brain of a subject. The methods include: providing pre-operative high-resolution MRI images of a brain of a patient segmented with three-dimensional surface conformable mesh representations comprising mesh elements to show respective segmented patient-specific brain structures; defining a target treatment region comprising a first one of the three-dimensional surface conformable mesh representations; defining a safety zone comprising a second one of the three-dimensional surface conformable mesh representations that is outside the target treatment region; obtaining high-resolution MRI images during the in vivo thermal treatment; and providing visualizations to a display that show thermally treated volumes and/or sub-volumes within the first and second three-dimensional surface conformable mesh representations color mapped to temperature during the in vivo thermal treatment.

The method can include calculating a distance of at least one of the mesh elements of the second mesh representation from the first mesh representation and/or a trajectory line of a laser providing the thermal treatment.

The method can include determining temperatures at different mesh element locations of the first and second mesh representations at different successive times during the in vivo thermal treatment for the visualizations.

The thermal treatment can be an ablation and the provided visualizations can show increased volumes of ablated tissue over time as the thermally treated volumes or sub-volumes and functional integrity/connectivity of ablated regions during the in vivo thermal treatment.

The thermal treatment can be a laser interstitial thermal therapy (LITT).

Each mesh element can include at least a first vertex, a second vertex and a third vertex surrounding a mesh face and the computer system can be configured to map measured temperatures to different mesh faces of the mesh elements.

The safety zone can be defined, at least in part, using vertex coordinates in MR imaging space of at least one of the mesh elements of the second mesh representation and a distance of the at least one the mesh elements from either a neighboring segment of the first mesh representation or a distance to a trajectory line of a thermal treatment device providing the thermal treatment or distances from both the first mesh representation and the trajectory line.

The safety zone can be identified and/or defined, at least in part, based on a location of at least one of the mesh elements or a vertex location of the at least one of the mesh elements corresponding to the mesh element that is closest to the first mesh representation and/or that is closest to a trajectory line of a thermal treatment device providing the thermal treatment.

The safety zone can be identified and/or defined, at least in part, using a distance of a virtual line that is normal to a surface defined by one or more of the mesh elements. The mesh elements can be triangular mesh elements, each having three vertices.

The provided visualizations can be configured to show thermally treated volumes and/or sub-volumes within the first and second three-dimensional surface conformable mesh representations, color mapped to temperature during the in vivo thermal treatment and texture mapped to mesh vertices or faces of the treated region.

The thermally treated volumes/sub-volumes can be visualized as treated volumes on their boundary surface(s).

These and other embodiments will be described further below.

BRIEF DESCRIPTION OF THE DRAWINGS

FIGS. 1A-1D are prophetic MRI-derived visualizations of a brain of a patient with patient specific shape-constrained segmentation of structures of the brain according to embodiments of the present invention.

FIG. 12A illustrates an example of color mapping of the thermal treatment. FIG. 12B illustrates texture mapping.

DETAILED DESCRIPTION

Figure 2:
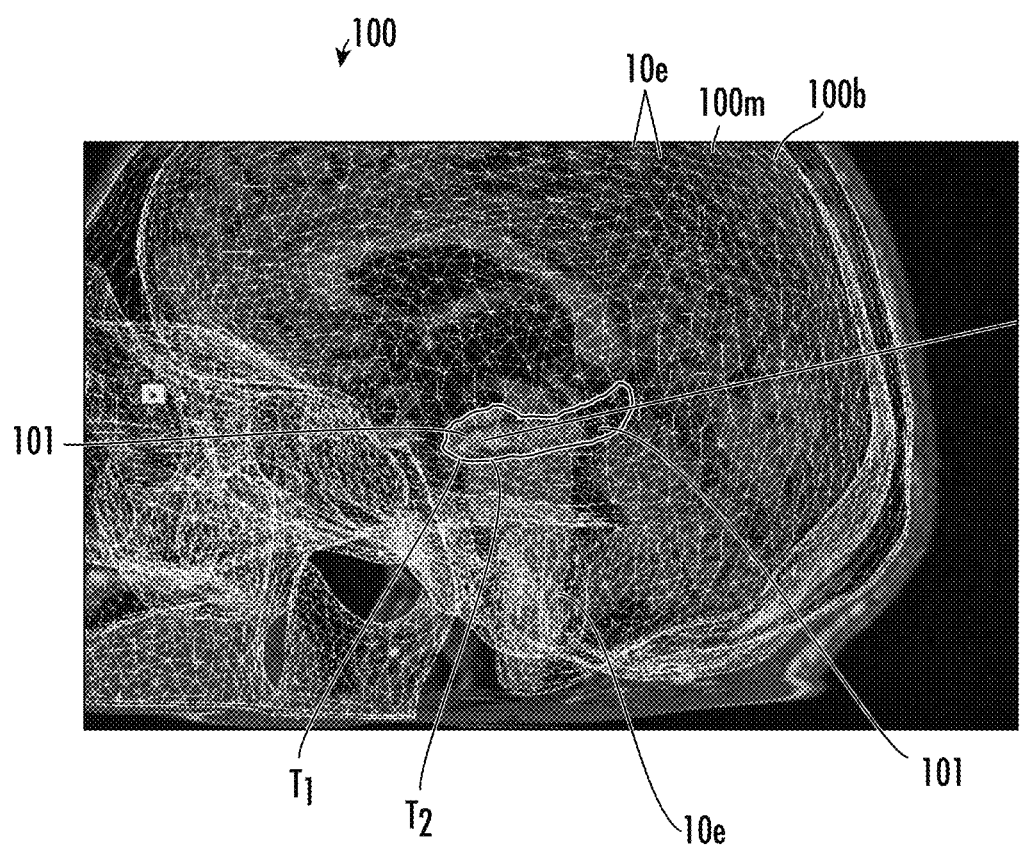
FIG. 2 is a prophetic three-dimensional brain (mesh) model of a brain of a patient comprising an amygdala and hippocampus segmented in a T1W scan/MRI image according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout. The abbreviation "FIG." may be used interchangeably with "Fig." and the word "Figure" in the specification and figures. It will be appreciated that although discussed with respect to a certain embodiment, features or operation of one embodiment can apply to others.

In the drawings, the thickness of lines, layers, features, components and/or regions may be exaggerated for clarity and broken lines (such as those shown in circuit of flow diagrams) illustrate optional features or operations, unless specified otherwise. In addition, the sequence of operations (or steps) is not limited to the order presented in the claims unless specifically indicated otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

The term "computer system" refers to any computer system and can include one or more processors, databases and servers. The computer system can comprise a local area network (LAN), a wide area network (WAN) and/or the internet. The computer system can comprise and/or be provided as a cloud computing resource. The computer system can comprise software and hardware and can reside at least partially on a workstation of a surgical planning and/or image-guided surgical system.

The term "brain atlas" refers to a digital model of features of a brain, human brain for human uses and animal brains for respective animal uses. The planning system can be independent of any particular atlas. One example brain atlas is the WayPoint™ Navigator Software (manufacturer: FHC) which has an integrated brain atlas to assist with surgical planning and predictive modelling for DBS, LITT and epilepsy procedures. See, https://www.fh-co.com/product/waypoint-navigator-software. Another example is the NeuroQuant® Software (manufacturer: Cortech Labs) which has an integrated brain atlas to automatically detect 3D anatomical structures from MR scans for purposes of planning and neurological assessment. See, https://www.cortechslabs.com/products/neuroquant/#. Both links were accessed as of Apr. 30, 2020. The contents of the noted websites are hereby incorporated by reference as if recited in full herein. The brain atlas can be linked or referenced rather than included in an onboard library of the surgical planning system.

The term "ACPC coordinate space" refers to a right-handed coordinate system defined by anterior and posterior commissures (AC, PC) and Mid-Sagittal plane points, with positive directions corresponding to a patient's anatomical Right, Anterior and Head directions with origin at the mid-commissure point.

The term "thermal" with respect to the medical procedure and/or surgical therapy device includes, but is not limited to, an ablation device such as a laser, a hyperthermia device and a hypothermia device.

The term "grid" refers to a pattern of crossed lines or shapes used as a reference for locating points or small spaces, e.g., a series of rows and intersecting columns, such as horizontal rows and vertical columns (but orientations other than vertical and horizontal can also be used). The grid can include associated visual indicia such as alphabetical markings (e.g., A-Z and the like) for rows and numbers for columns (e.g., 1-10) or the reverse. Other marking indicia may also be used. The grid can be provided as a flexible patch that can be releasably attached to the skull or scalp of a patient. For additional description of suitable grid devices, see co-pending, co-assigned U.S. patent application Ser. No. 12/236,621, the contents of which are hereby incorporated by reference as if recited in full herein.

The term "fiducial marker" refers to a marker that can be electronically identified using image recognition and/or electronic interrogation of image data. The fiducial marker can be provided in any suitable manner, such as, but not limited to, a geometric shape of a portion of the tool, a component on or in the tool, a coating or fluid-filled component or feature (or combinations of different types of fiducial markers) that, for MRI/CT uses, makes the fiducial marker(s) visible in a respective imaging modality with sufficient signal intensity (brightness) for identifying location and/or orientation information for the tool and/or components thereof in space.

The terms "RF safe" and "MRI compatible" means that the so-called component(s) is safe for use in an MRI environment and as such is typically made of a non-ferromagnetic MRI compatible material(s) suitable to reside and/or operate in a high magnetic field environment, without inducing unplanned current that inadvertently unduly heats local tissue or otherwise interferes with the planned therapy.

The term "high-magnetic field" refers to field strengths above about 0.5 T, typically above 1.0 T, and more typically between about 1.5 T and 10 T, including 3 T systems. MRI Scanners are well known and include high-field closed bore and open bore systems.

The term "near real time" means that (MR) image data is obtained during a thermal treatment (e.g., concurrent imaging and ablating) without requiring contrast enhancements and a corresponding image and/or visualization using the obtained (MR) image data is presented on a display within between about 1 millisecond to less than about 10 seconds from the time of the data acquisition. Typically, the image data is obtained while the thermal treatment is ongoing and a corresponding rendered image and/or visualization(s) is generated and displayed in a range of about 1-7 seconds. The imaging and visualizations can be sequentially generated during the thermal treatment with minimal latent time between serial image acquisitions.

Generally stated, embodiments of the present invention provide systems, methods and computer program products that can be configured to leverage geometry of defined, adjacent brain structures segmented with a shape-constrained deformable brain model in a high resolution preoperative image volume. Embodiments of the present invention can employ patient-specific anatomical structures as boundary conditions, that can be defined and/or set by a clinician operator and used for controlling energy delivery during a thermal treatment such as an ablation. Thermal treatments occur in three dimensions not two dimensions, so setting safety zones/temperature guards or other boundary conditions in three dimensions provides for an advanced safety feature and for selective thermal treatments.

As is well known to those of skill in the art, the term "segmented" means partitioning an image into various subgroups of pixels to define image objects/brain structures of interest. The segmentation can identify boundaries, draw lines, and separate target structures or objects in an image from less relevant structures or objects. See, e.g., Weese, J., Wächter-Stehle, I., Zagorchev, L. and Peters, J., 2014. *Shape-constrained deformable models and applications in medical imaging. In Shape Analysis in Medical Image Analysis* (pp. 151-184). Springer, Cham., the contents of which are hereby incorporated by reference as if recited in full herein.

The term "high-resolution" with respect to the MRI images means isotropic voxel size in a range of 0.5 mm and 1 mm. The term "high-resolution" with respect to the mesh models means that each mesh element thereof has a small sub-millimeter area $<1$ mm$^2$ and/or volume $<1$ mm$^3$.

A three-dimensional brain model 100 can be adapted to the MRI data to extract patient-specific geometry of target brain structures such as cortical and sub-cortical brain structures. MRI images and segmented with the (shape-constrained, deformable) brain model can be used to identify boundaries of target intrabrain structures 101 such as the thalamus.

FIGS. 1A-1D are prophetic color-coded brain visualizations 100 of a brain of a patient with a brain model 100m and segmented adjacent brain structures 101, each segmented brain structure 101 can be shown in a different color and in different two-dimensional (slice) views and at least one three-dimensional view. FIG. 1A is an example three-dimensional view and FIGS. 1B-1D are example two-dimensional views.

FIG. 2 illustrates an example brain visualization 100 with a mesh model 100m that includes mesh representations 101 (color-coded) of anatomical structures, shown as brain structures comprising the amygdala and the hippocampus, segmented in a T1W scan of an MRI brain image 100b of a patient. The mesh models 100m can be surface conformable mesh models 100m of respective segmented brain structures 101. The mesh models 100m can have contiguous sets of mesh elements 10e. Each of the mesh models 100m of a respective segmented brain structure 101 can be shown with a different color perimeter line 101p and/or corresponding color volume. Different mesh representations 101 of brain structures within the mesh model 100*m* can be encoded with a baseline and/or target thermal treatment temperature $T_1$, $T_2$. The target thermal treatment temperature can be a maximum and/or a minimum temperature or other defined temperature. The term "encoded" means that a temperature (s) is defined and attached to a particular mesh model 100*m* and/or locations of mesh elements 10*e* of a respective mesh model 100*m*.

Figure 3A:
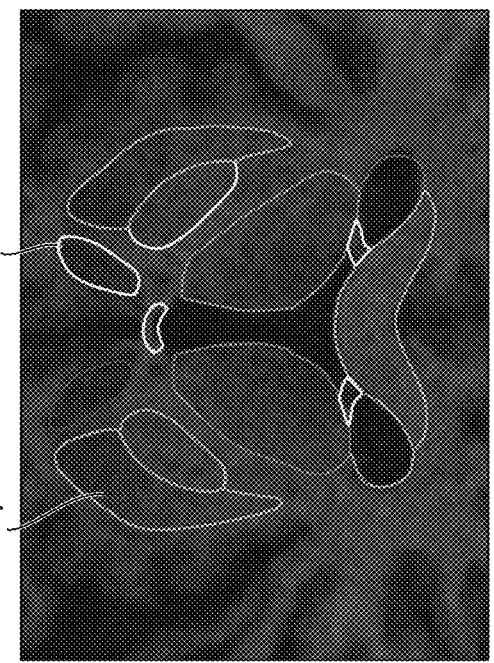
FIGS. 3A-3D are prophetic MRI-derived visualizations of a brain with segmented three-dimensional target treatment structures and adjacent segmented avoid structures according to embodiments of the present invention.
Figure 3B:
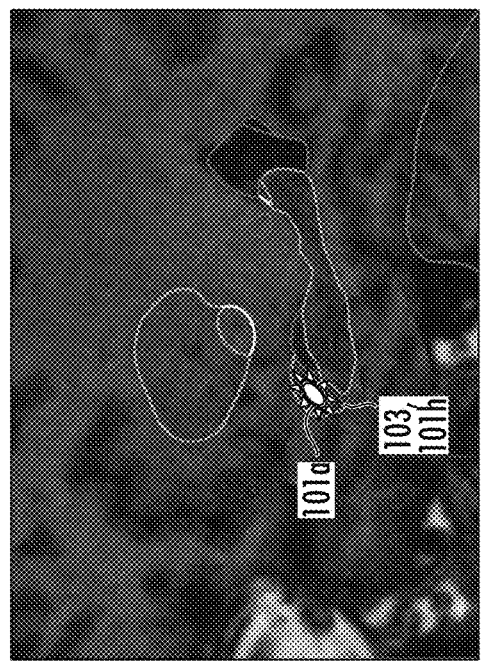
Figure 3C:
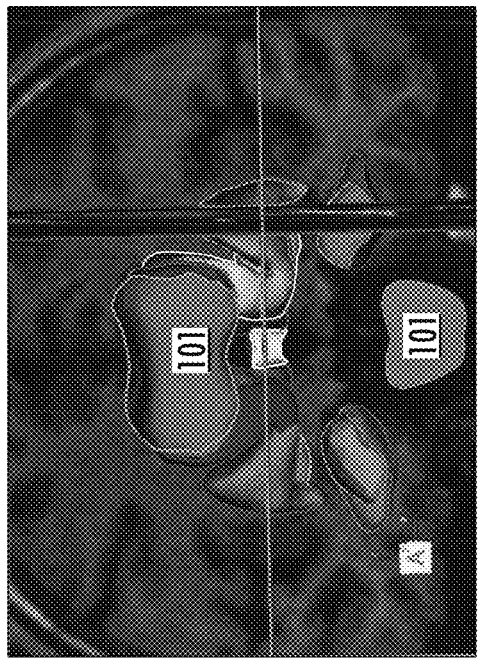
Figure 3D:
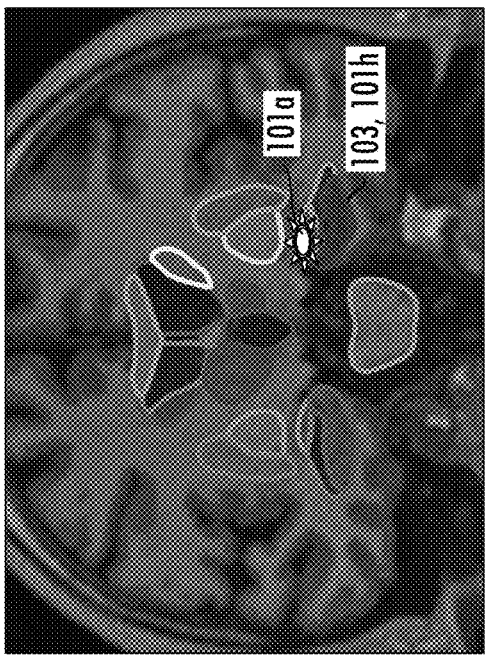

FIGS. 3A-3D illustrate a prophetic example of patient-specific segmented brain structures 101 that can be used for guiding thermal treatment (e.g., ablation) of the amygdala 101*a* as a first one of the segmented brain structures 101, shown with the red "sun" with white circle perimeter outline with sun spikes in FIGS. 3C and 3D. A second three-dimensional-segmented mesh represented structure 101, shown as corresponding to the hippocampus (blue outline) 101*h* can be identified as a "safety zone" 103 and used to inform when to cease thermal energy delivery when a perimeter boundary of the hippocampus 101*h* reaches a defined temperature. This allows for selective thermal treatment, e.g., ablation of only the amygdala 101*a* in this example.

It can be important to control the delivery of energy/therapy, such that the treatment region, e.g., forming a lesion or ablation, by way of example, can be contoured according to the desire of the clinician/operator. This may be facilitated by informing and/or automatically ceasing energy delivery when operator-defined or otherwise identified patient-specific anatomical "safety zone" 103 (e.g., a tissue boundary) exceeds a baseline temperature and/or a defined temperature threshold.

The term "safety zone" 103 is used broadly herein to refer to one or more points, lines, curves, regions, shells, areas, volumes and the like in a patient that is not the target thermal treatment region but that may be relevant for sensitive tissue or nerve areas or for its proximity to the target thermal treatment region of trajectory path thereto. A safety zone 103 can be contoured to patient-specific anatomy and/or a specific thermal treatment. Anatomical structures 101 used for setting or defining a safety zone 103 may be clinician/operator-defined using a region- or volume-of-interest (ROI or VOI) software tool or otherwise identified and defined, for example automatic anatomical segmentation. Safety zones 103 may also be identified and/or defined through the use of multi-modal integration (e.g., one or more of MRI, CT, DTI, SEEG, MEG, MR spectroscopy, etc.) information. For example, identifying where fiber tracts pass through a brain structure exist, safety zones 103 can be set or defined for a particular patient, particularly where such a sensitive brain structure may reside adjacent or in close proximity to a thermal treatment trajectory line. The term "safety zone" refers to non-target tissue and/or sensitive tissue that is to be avoided during a thermal treatment by the treatment device and/or its thermal output, e.g., "no-go" regions in the brain.

Pre-defined, automatically (non-clinician/operator) identified structures 101 may be recommended to the operator as ROIs or VOIs for safety zones 103. The perimeters, borders and/or interfaces with other identified structures 101 of these patient-specific anatomical structures 101 may then be chosen or removed as a safety zone(s) 103, where the clinician/operator wishes to cease thermal (energy) delivery or by "standard of care" default for a defined medical procedure when a respective safety zone 103 approaches, exceeds, or falls below specified temperatures.

In some embodiments, a clinician/operator can select or pre-set one or more patient-specific segmented anatomical structures 101, shown as a mesh model in 2D and/or 3D, during a pre-plan operation using a User Interface (UI) 301 (FIG. 6A) to define a safety zone 103 as a boundary outside the target treatment region when performing a thermal treatment such as an ablation or lesion and/or either hyper- or hypothermal treatments.

Additionally, having identified where the safety zone(s) 103 is/are in relation to the intended lesion/ablation target(s), the systems, methods and processing circuits (e.g., comprising software) can provide patient-specific imaging planes to best monitor the thermal treatment during treatment, e.g., allowing near real time visualizations of the lesion or ablation progress using, for example, MR thermometry. Near-real time MRI imaging for showing/monitoring thermal treatment progress may occur in 2D plane(s) and/or 3D volume(s) capturing both the safety zone(s) 103 and target treatment region such as a lesion/ablation target(s).

Using patient-specific anatomical structures 101 as boundary conditions, especially those segmented and in 3D, may be a leap forward from known current technology where only 2D ROIs, set by the operator, are used for controlling energy delivery during an ablation. Ablations occur in 3D, not 2D, so setting safety zones/temperature guards or other boundary conditions in 2D can be problematic. Setting boundary conditions in 3D can provide for an advanced safety feature and for selective thermal treatments such as ablations or lesions to be created.

As the operator changes perspectives on imaging planes, especially in oblique 2D acquisitions of anatomy, it is easy to lose track of where the target is relative to the ablation. Tracking and utilizing, in 3D, patient-specific anatomy aids in the safe delivery of energy to create an ablation. More specifically, aids the operator in preventing too large of an ablation.

Multi-modal integration can allow for more-precise thermal treatments such as ablations to take place. In neurosurgery, specifically, the use of DTI for example may allow the operator to identify specific fiber tracks to safeguard.

Tracking, in 3D, how the thermal treatment is proceeding by monitoring how the temperature is approaching the "safety zone" 103 may allow for the proactive cessation of energy delivery, as opposed to reactive.

Although primarily described herein with respect to the brain, it is contemplated that embodiments of the invention are also useful for other medical treatments and associated anatomy (e.g., cardiac, neuro, prostate, pancreas, liver, etc.). Also, other imaging modalities may be used alone or in combination with MRI to carry out the thermal treatment(s).

Image data obtained in near-real time can provide be used to provide "live" or successive "near-real time" updates during an intra-brain surgical-guided MRI procedure whereby visualization of the thermal treatment, such as, for example, an ablation, in both regions with temperatures of each differentiated to correspond to actual temporally present temperatures can be shown concurrently in a patient being treated for a medical condition such as, by way of example only, Epilepsy.

Quantitative indices can be determined and/or measured within an anatomical structure and/or at one or more 3-D locations of respective mesh vertices 10*v* (FIG. 4) (e.g., the temporally current intrabrain temperature) and this information can be used to assess the procedure in near-real time, as a respective thermal treatment progresses during the procedure such as an actual ablation.

Embodiments of the present invention can be configured to provide calculated, quantitative indices of temperature and/or thermal treatment coverage of one or more of the brain structures 101 in near real-time and/or provide near real-time visual and quantitative feedback to a clinician operator during a respective active thermal procedure, such as during an LITT MRI-guided surgical procedure of the brain.

Embodiments of the present invention are configured to provide methods for quantitative assessment of a thermal procedure, such as a LITT procedure, using a correlation of a pre-planned ablation volume of one or more target brain structures 101 and defined planned ablation temperature(s) to corresponding volumes of the target brain structures and temperature measurements during the thermal treatment within the targeted brain structures 101.

Thermally treated volumes can be estimated within segmented brain structures 101 by detecting phase data and/or intensity changes of pixels/voxels of MRI image data within those regions with respect to the baseline values of those pixels/voxels in the pre-operative brain MRI 100 (FIG. 1A).

Figure 4:
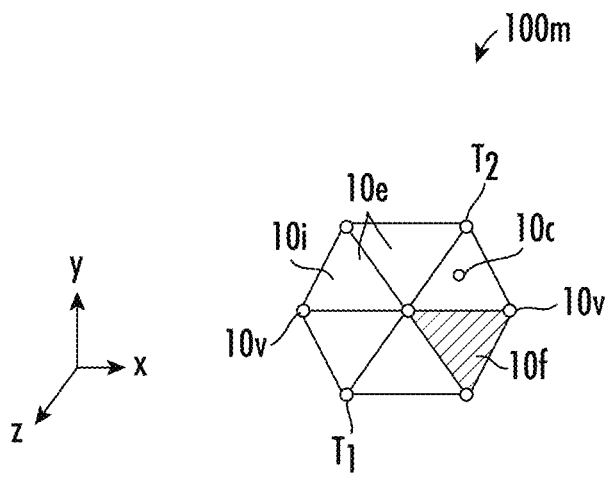
FIG. 4 is an enlarged example of a sub-set of mesh elements that can be applied to segmented brain structures according to embodiments of the present invention.

Referring to FIG. 4, the mesh model 100$m$ can be a mesh brain model with mesh elements 10$e$. The mesh elements 10$e$ can be contiguous mesh elements 10$e$. Different segmented and mesh represented structures 101 can have the same size or differing size mesh elements 10$e$. The mesh elements 10$e$ can be triangular mesh elements, each having three vertices 10$v$. As shown, some of the neighboring mesh elements can share one or more vertices 10$v$.

Defined thermal treatment temperatures $T_1$, $T_2$ (e.g., ablation temperatures) can be encoded onto the mesh represented structures 101 of the mesh model 100$m$ (FIG. 2).

Referring to FIGS. 2 and 4, the mesh model 100$m$ can provide the segmented mesh representations 101 with contiguous mesh elements 10$e$ covering each target mesh representation structure 101 and optionally the outer surface of the brain as well.

The segmentation can be carried out using a shape-constrained model and/or the mesh model 100$m$ can be provided as a shape-constrained model of segmented structures of the brain. See, WEESE et al. "*Shape-Constrained Deformable Models and Applications in Medical Imaging*" *Shape Analysis in Medical Image Analysis*, pages 151-184, Lecture Notes in Computational Vision and Biomechanics, Vol 14, Springer (2014), for further discussion of shape-constrained models for segmentation, the content of which is hereby incorporated by reference as if recited in full herein.

Referring to FIGS. 2 and 4, typically, a plurality of mesh elements 10$e$, each with a plurality of mesh vertices 10$v$ surrounding an interior region 101 with a conformable outer face/outer surface 10$f$, can cover or delineate a segmented (target brain) structure 101. The mesh elements 10$e$ can extend in three dimensions in a defined coordinate system, such as, X, Y, Z axes of an MRI imaging system.

Defined target thermal treatment temperatures $T_1$, $T_2$ (e.g., ablation temperatures) can be encoded on different mesh elements 10$e$ such as at different mesh vertices 10$v$ of a respective brain structure 101 and/or at different interior regions 10$i$ of respective mesh elements 10$e$ prior to a surgical procedure.

Intensity values of pixels in thermal images at the locations of mesh vertices 10$v$ of mesh elements 10$e$ can be monitored and visualizations of present thermal temperatures can be color mapped to the surface(s) of a segmented structure 101 and corresponding mesh model 100$m$.

Color mapping can be carried out assuming the same color for an entire related mesh structure, volume and/or region. Texture mapping can assign different colors to mesh vertices and/or faces of the mesh elements.

Quantitative indices derived from the geometry of the mesh representation in the image(s) can be used to correlate the different images and register the segmented brain structures 101. The quantitative indices can include, for example, coordinates of mesh vertices, centers of mass 10$c$, moment invariants, principal curvature of the mesh representation and/or mesh elements thereof, surface derivatives, etc. The mesh elements 10$e$ can be triangles that can adapt to similar intensity values in different images. The vertices 10$v$ of respective mesh elements 10$e$ can be pulled to the same intensity values in different successive scans, that can enforce point-based correspondence between mesh elements 10$e$, such as points of triangular vertices The mesh geometry of a particular mesh representation 101 depends on the modeled structure (segmented brain anatomy). The mesh geometry of one or more mesh represented structures 101 for temperature monitoring can be used to identify a set of vertices 10$v$ from the mesh representation 101 and monitor those for temperature changes at their corresponding locations. These can be configurable. If these vertices 10$v$ as "safety points" are selected on the mean mesh representation 101, which is the mesh representation before adaptation to a specific scan, the locations of these vertices 10$v$ of corresponding mesh elements 10$e$ can adapt to their corresponding locations in newly acquired patient image data, advantageously providing reproducible temperature monitoring at the same anatomical locations in different patient scans.

A safety zone(s) 103 can be defined using mesh geometry of a respective mesh represented structure 101 of the mesh model 100$m$ (e.g., vertex coordinates, distance from trajectories, distance along triangle normals, and any other derivatives of mesh geometry). The thermal treatment (e.g., ablation) temperature can be displayed in texture (color) mapped to the outer surface of the mesh representations of one or more segmented structures 101. The texture mapping can be texture mapped to mesh vertices or (boundary) faces of the thermally treated volume(s) and/or sub-volume(s) of the target treatment region.

The thermal ablation can change the intensity values of ablated tissue. The intensity values of the image at locations of mesh vertices 10$v$ can be monitored and visualizations can be generated of a present ablation temperature as texture mapped to the mesh structure 101 and/or volumes or sub-volumes of tissue corresponding to the mesh represented structure 101.

The mesh model 100$m$ can be a high-resolution mesh representation. Each mesh element 10$e$ of a target segmented mesh represented (brain) structure 101 can have a surface area that is less than a millimeter, such as a surface area in a range of 0.01 mm and 1 mm, for sub-millimeter resolution.

The mesh representation 101 can be a surface conformable mesh representation that conforms to the surface shapes of respective segmented brain structures. Respective mesh elements 10$e$ can deform, e.g., grow or shrink, so that the corresponding boundary (outer surface) in a mesh representation 101 can cover a respective segmented brain structure 101 in three dimensions.

During a thermal treatment such as, for example, an ablation procedure, temperature can be determined and/or measured at the same mesh element 10$e$ locations over successive image acquisitions and more easily correlated to position in 3-D imaging space for improved accuracy/reliability.

A visual (thermal) map can be fitted to provide a thermal color mapped/coded overlay and/or visualization of a brain structure 101 using a few temperature measurements corresponding to and/or obtained from a subset of mesh elements 10e, or portions thereof, such as mesh vertices 10v, of mesh representations of structures 101 for near real-time (e.g., almost immediate) visual and quantitative feedback to a neurosurgeon.

Figure 10A:
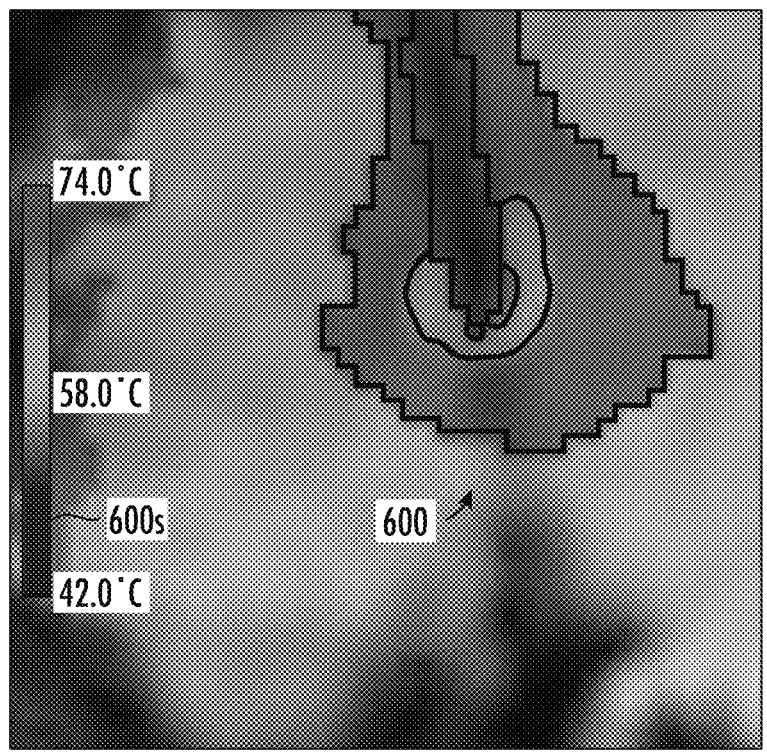
FIGS. 10A and 10B are example schematic illustrations of thermal map overlays showing temperature variation of tissue color coded to thermal temperatures according to embodiments of the present invention.
Figure 10B:
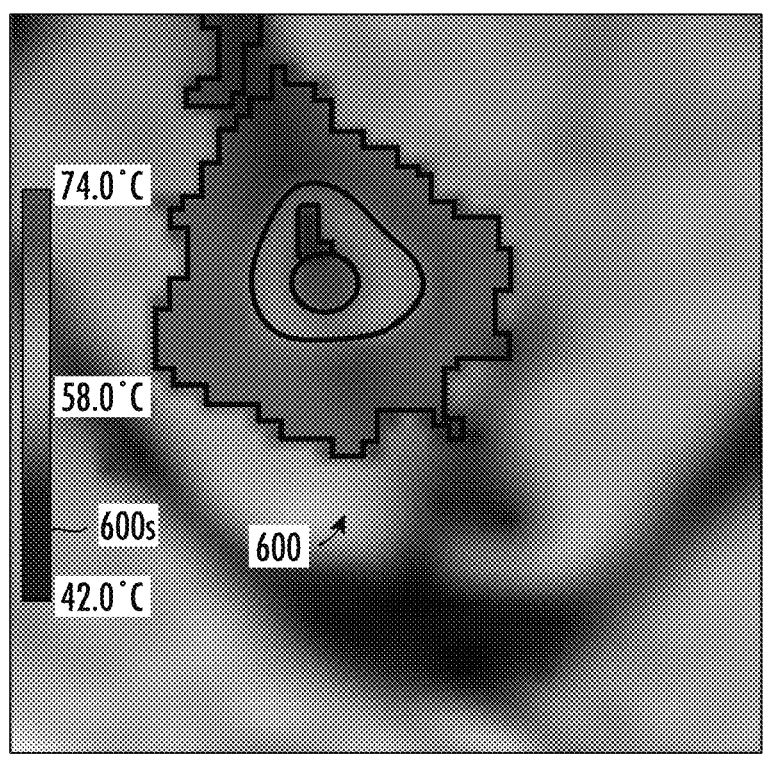

Referring to FIGS. 10A, 10B, a multi-color overlay or thermal status visualization map 600 can be used to visualize the thermal treatment (e.g., ablation) within a targeted region and outside thereof based on measurements derived at the 3-D location of mesh vertices 10v.

Temperature and locations thereof corresponding to the mesh vertices 10v can be measured in a number of ways as is known to those of skill in the art. By way of example, MR thermometry can be used using any suitable MR thermometry software such as the ThermoGuide™ software from Image Guided Therapy (IGT), France. See, also, McNichols et al., *MR thermometry-based feedback control of laser interstitial thermal therapy at 980 nm*; Lasers Surg. Med. 2004; 34(1): 48-55, doi: 10.1002/lsm.10243, PMID: 147555424, the contents of which are hereby incorporated by reference as if recited in full herein.

Embodiments of the invention can be configured to provide systems/methods/image processing circuits that can display volumes and/or areas of tissue thermally treated using color-mapping or other visual indicia to represent baseline versus change in temperature or change in tissue status in response to thermal treatment.

For example, within a targeted segmented mesh representation of a (brain) structure 101 and/or about 3-D surface locations thereof, a first color such as green can represent tissue that has not been thermally treated (e.g., ablated), a second color such as yellow can represent tissue that is partially treated tissue (reversible tissue damage), and a third color such as red, can represent permanently treated tissue (e.g., ablation, cryogenic or other thermal treatment resulting in necrotic or irreversible tissue damage).

The differentiation of tissue having different thermal exposures due to the thermal treatment can be shown on a display 300d (FIGS. 6A, 8, 10A, 10B, 11A, 11B, for example). The differentiation can be determined in a number of ways, e.g., near real-time analysis of spatial and temporal statistics from the image data (including but not limited to histogram analysis), pixel and/or voxel intensity, impedance measurements, and the like or combinations of the above.

In some embodiments, a temporal and/or spatial change of one or more parameters of pixels/voxels at locations of different mesh elements 10e corresponding to tissue during the thermal treatment can be determined and used to identify temperature change from baseline. A change in a pixel/voxel value corresponding to tissue of one or more mesh elements 10e in a target treatment region and/or brain structure 101 can be determined using histograms or other parameters such as gradient, intensity, pattern, texture, relative to pre-operative planning image with the acquired patient-specific image data of tissue features (whether the tissue has fibers, vasculature (blood flow), tissue elasticity, perfusion characteristics, and the like).

Embodiments of the present invention can provide methods, systems and circuits configured to generate near-real time intra-procedural, quantitative visualization of ablation derived from intra-operative MRI. Pre-planned ablation volumes and ablation temperature(s) and safety zone 103 temperature(s) can be correlated to the near-real time information and performed with respect to intra-procedural MRI acquired during a LITT procedure.

In some embodiments, a quantitative thermal ablation score can be calculated. For example, a numerical score can be provided that evaluates well an ablation was performed based on the ablated volume, reached temperature at safety points, and other quantitative data that correlates to a successful treatment.

Embodiments of the present invention can provide thermal and functional outcome prediction based on measured quantitative indices from intra-operative MRI. Quantitative indices may include measured volume, measured temperature, intensity changes, etc. and/or other quantitative information derived from the images during a thermal treatment such as during an ablation.

Such quantitative measurements from a pre-plan and corresponding intra-procedural values can be correlated with functional outcomes and used to build a machine learning or artificial intelligence classifier based on prior post-outcome data that can provide patient-specific outcome prediction.

Embodiments of the invention can generate near-real time visualization of tissue ablation during LITT. Thermal measurements at surface vertices 10v can be texture-mapped to triangular mesh elements 10e to visualize the state of ablation in 3-D with respect to the treated, and untreated "safety zone" patient-specific anatomy.

The mesh model and temperature monitoring using same can be applied to any thermal treatment in the brain, e.g., brain tumors, epileptic foci, etc.

The brain segmentation can be carried out in different manners. For example, automatic segmentation of a volume of interest using a seed point, manual painting using a "smart brush", etc.

If a procedure is performed in the Operating Room (OR) rather than an MRI suite, other imaging modalities (e.g., CT) can be used to measure temperature and estimate ablated volume and MR thermometry is not required.

Embodiments of the invention can include a smart planning feature based on the segmented mesh representation(s) 101 and pre-defined target treatment region (e.g., ablation ROI) identified by the surgeon. Such features can allow the clinical team to visually assess ideal stereotactic laser ablation (SLA) parameters such as: laser fiber type, trajectory choice (possibly multiple trajectory) or the necessary fiber retraction to cover the desired ROI.

Figure 5A:
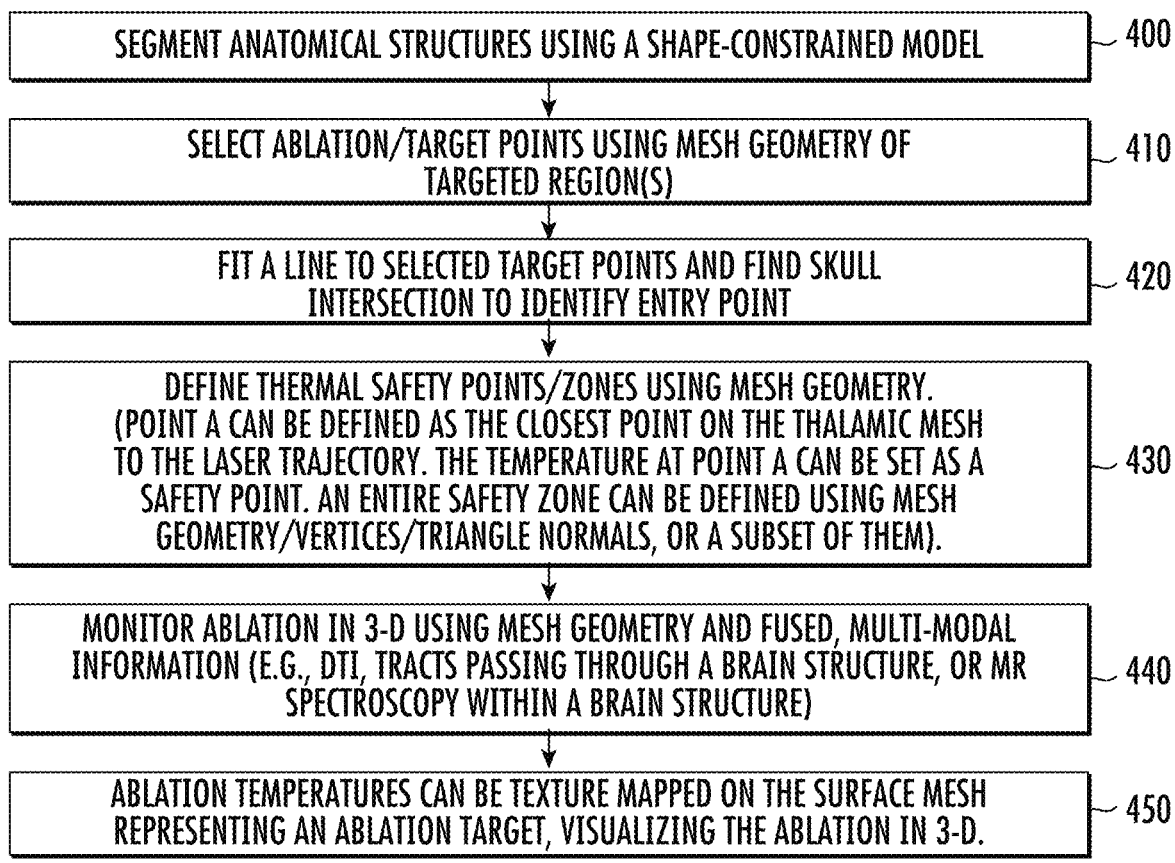
FIG. 5A is a flow chart of example actions that can be used to carry out a thermal treatment according to embodiments of the present invention.

FIG. 5A illustrates a set of actions/steps that can be used to facilitate a thermal treatment. Anatomical structures (in a high resolution pre-operative brain image) can be segmented, optionally using a shape-constrained model (block 400). Surface conformable mesh representations can be applied to the segmented structures. Target thermal treatment points can be selected/defined using mesh geometry of a target treatment region(s) (block 410). A trajectory path Pt through a skull can be generated/selected to one or more target points to reach the target thermal treatment points and extend through an entry location in the skull S (block 420). One or more thermal safety points/zone(s) can be identified using mesh geometry of a structure of interest, typically adjacent or neighboring the target treatment region or trajectory path Pt and associated with a sensitive tissue or nerve (block 430). For example, a point closest to the trajectory path Pt (point A, FIG. 6D) outside the target thermal treatment region, e.g., a thalamic mesh representation can be defined as the safety zone 103 or as a point of interest in the safety zone 103. Point A can be associated with a particular mesh element or vertex thereof. The temperature at point A can be monitored. An entire safety zone 103 can be defined using 3-D mesh geometry/vertices/triangle normals, or a subset of such mesh features, over an entire or part of a structure 101. The thermal treatment is monitored in near real-time in 3-D using mesh geometry of the structure. Visualizations using fused, multi-modal information (e.g., DTI, tracts passing through a brain structure, or MR Spectroscopy within a brain structure) can also be used.

Ablation temperatures can be texture/color mapped on the conformable surface mesh representations representing a thermal treatment target (e.g., ablation target) and visualizations of the ablation in 3-D can be provided (block 450).

Figure 5B:
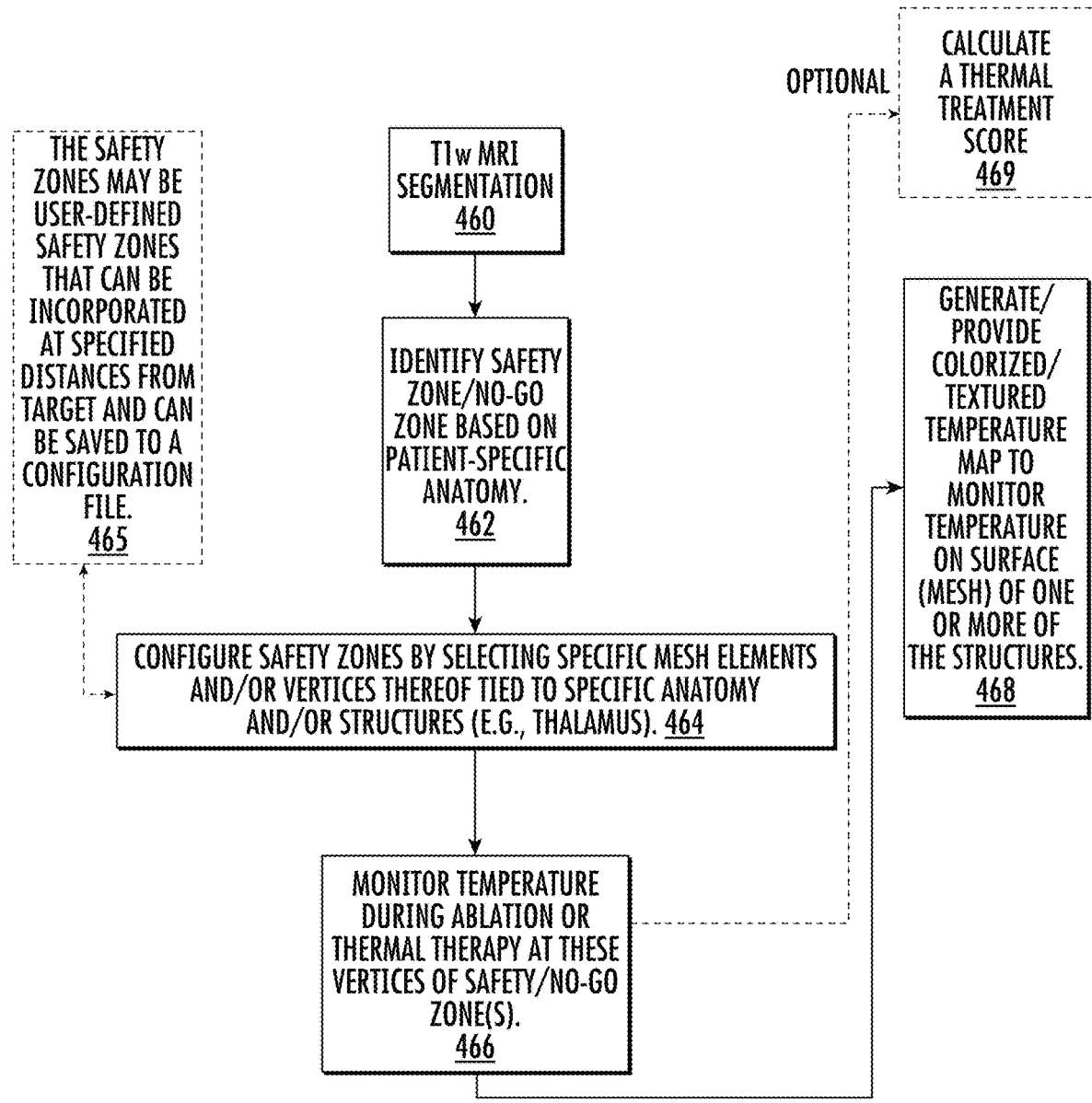
FIG. 5B is a flow chart of example actions that can be used to facilitate a thermal treatment according to embodiments of the present invention.

FIG. 5B illustrates actions that can be used to facilitate a thermal therapy. An image of a brain of a patient can be segmented for T1w MRI segmentation (block 460). Safety zone/no-go zone(s) can be identified based on patient-specific anatomy (block 462). Safety zones can be configured by selecting specific vertices tied to specific anatomy and/or structures (e.g., thalamus) (block 464). Temperature can be monitored during ablation or thermal therapy at these vertices of safety/no-go zone(s). (block 466).

The safety zones may be user-defined safety zones that can be incorporated at specified distances from target and can be saved to a configuration file. (block 465).

Colorized/textured temperature maps can be generated/provided to a display to monitor temperature on surface (mesh) of one or more of the structures. (block 468).

A thermal treatment score can be generated and provided to a display (block 469).

Figure 6A:
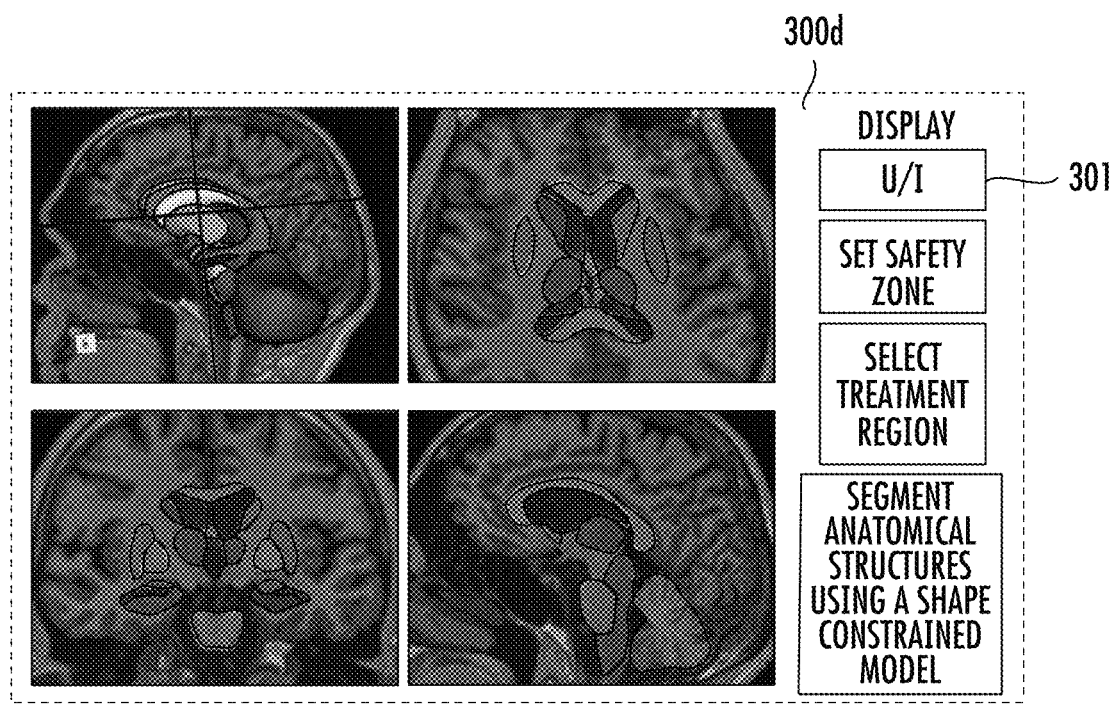
FIG. 6A is an illustration of an example display of visualizations of a panel of images showing segmented anatomical structures using a shape-constrained model according to embodiments of the present invention.

FIG. 6A illustrates a display 300d with brain images segmented with anatomical structures and providing a User Interface (UI) 301 having selectable user inputs to "set safety zone" and "select treatment region" both of which can be displayed using mesh representations of segmented structures 101.

Figure 6B:
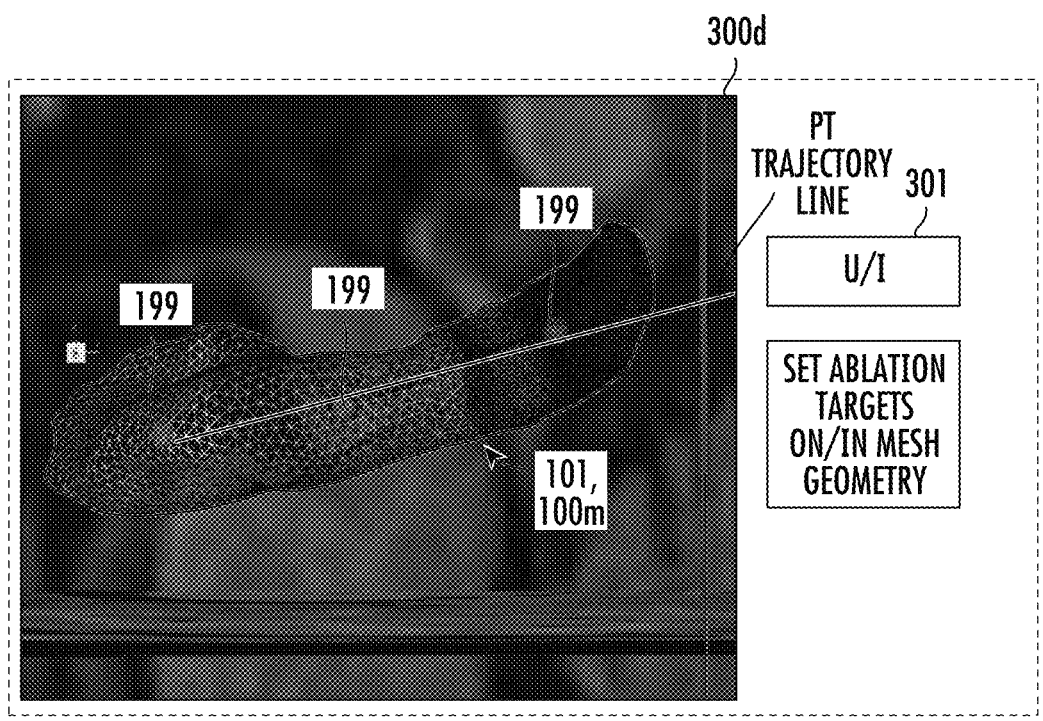
FIG. 6B is an illustration of an example display with an enlarged visualization of a target segmented anatomical structure with a shape conforming (surface) mesh model applied thereto and with target thermal treatment points defined using mesh geometry of the segmented anatomical structure according to embodiments of the present invention.

FIG. 6B illustrates an enlarged view of a target region of interest (ROI) shown as a segmented brain structure comprising a surface conformable 3-D mesh representation 101 and selected target thermal treatment points 199 along and in the ROI. The UI 301 can have a user input that allows a user to confirm and/or select/position the target thermal treatment points 199. The trajectory path Pt can connect the selected points 199.

Figure 6C:
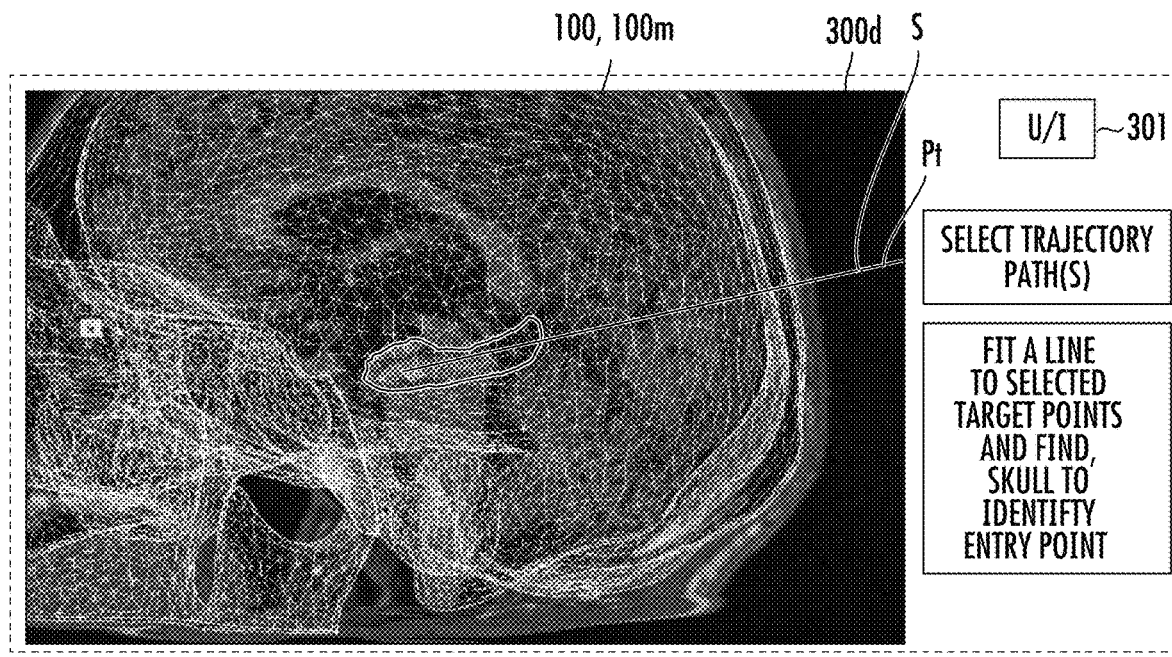
FIG. 6C is an illustration of an example display with a visualization of the brain with a trajectory line extending through a skull entry point to the target segmented anatomical structure shown in FIG. 6B according to embodiments of the present invention.

FIG. 6C illustrates that the UI 301 can allow a user to select a trajectory path Pt with a line that extends through the skull S to define a brain entry point. The selection input can be based on automatically proposed options or allow a user to select different positions that extend to the treatment points 199. For automated trajectory candidate planning options, see, e.g., co-pending U.S. patent application Ser. No. 17/232,429, the contents of which are hereby incorporated by reference as if recited in full herein.

Figure 6D:
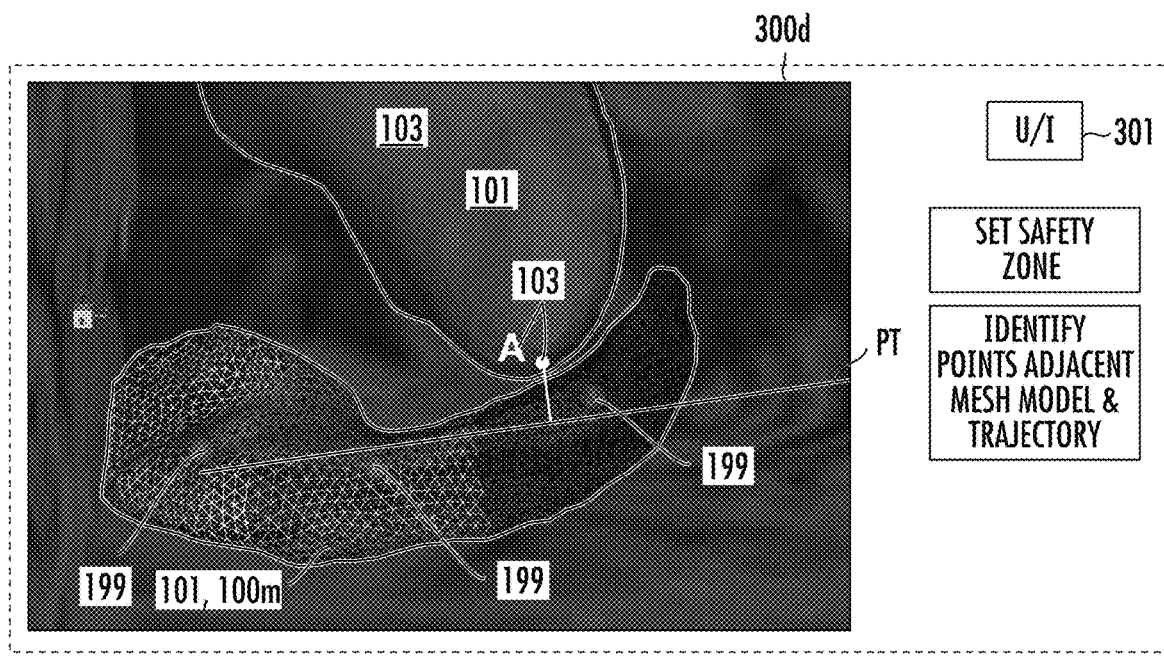
FIG. 6D is an illustration of an example display with enlarged visualization of the target segmented anatomical structure covered with the shape-conforming mesh model applied thereto and with a thermal (e.g., laser) trajectory line extending through the target anatomical structure used to define a first safety point (point A) outside the target treatment anatomical structure (or portion thereof) in close proximity to the trajectory line according to embodiments of the present invention.

FIG. 6D illustrates that the UI 301 can allow a user to select a safety zone 103 for monitoring temperature outside the target thermal treatment region. The safety zone 103 can comprise a point, point A, which is at a distance closes to the trajectory path Pt and outside the target ROI/anatomical structure shown with a respective mesh representation 101. The temperature at point A can be monitored as a safety check to ensure that this safety zone is not unduly impacted by the thermal treatment. The thermal temperatures during the thermal treatment can be monitored and provided as a color/texture mapped to the conformable surface mesh representing the target ROI and providing the visualization(s) in near real-time and in 3-D.

As will be discussed further below with respect to FIG. 8, embodiments of the present invention include an image-guided system 1000 with a trajectory guide 200 that can comprise at least one through channel that can be used to place the directional medical device 10. The system 1000 can use the deformable brain model 100 and/or mesh representation/model 100m.

Referring to FIGS. 7A-7D, an example trajectory guide 200 is shown. The trajectory guide 200 can have a base 110 that surrounds a patient access aperture 112. The trajectory guide 200 can have a platform 132 with a port 132p. A tubular member 204 can extend below the port 132p and terminate adjacent to and/or above the patient access aperture 112. Orientation indicia 132i can be provided on the platform 132 that can be painted, coated or otherwise provided with color-coded markings on an upper surface 132u of the platform 132 that can help a user to align the guide 211 and/or identify a channel and/or path selection.

Figure 7A:
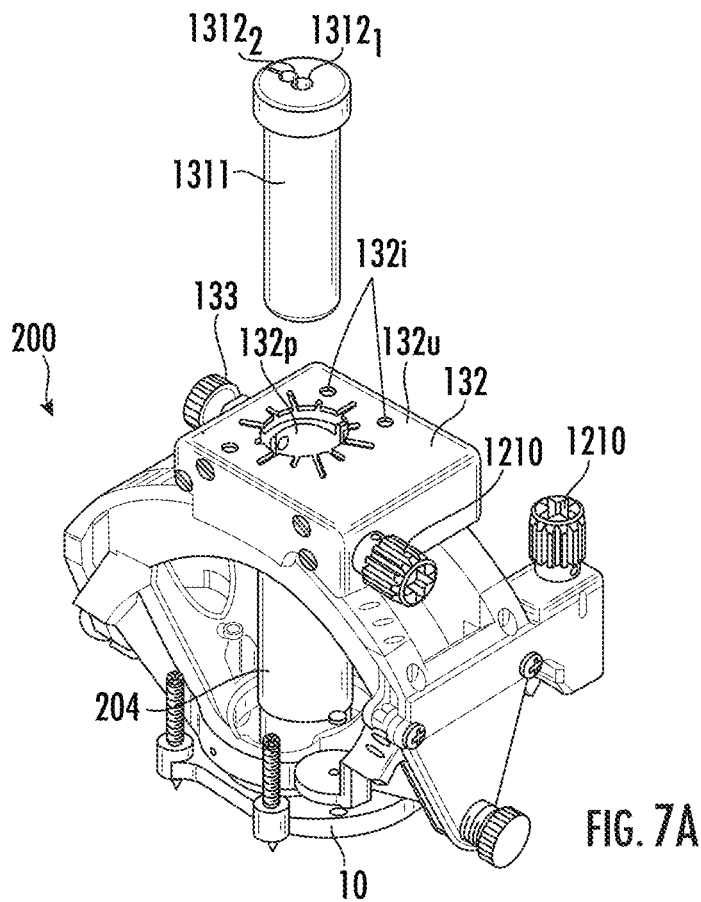
FIGS. 7A-7B are side perspective views of an example trajectory guide assembly with a rotatable offset trajectory guide coupler according to embodiments of the present invention.
Figure 7B:
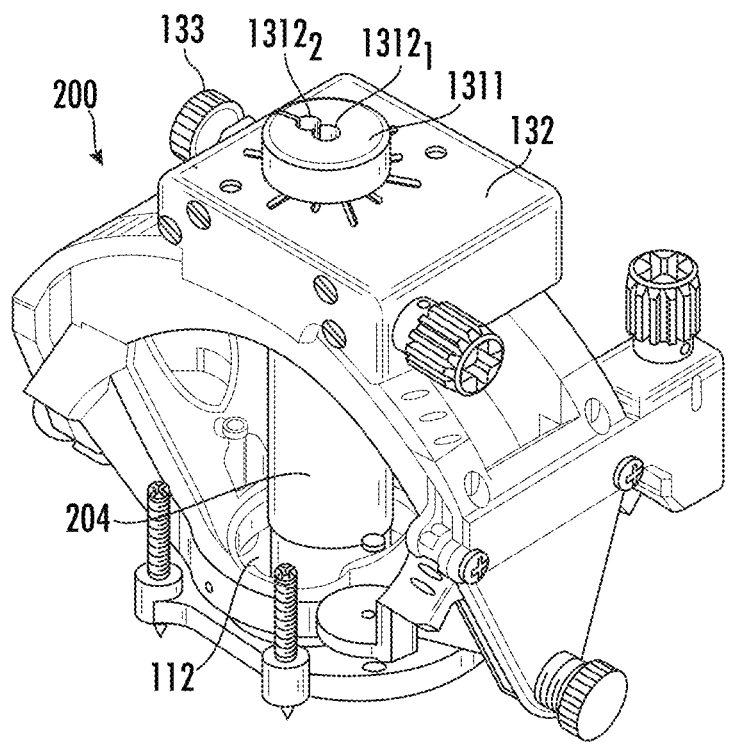

FIGS. 7A and 7B illustrate the use of a rotatable device guide 1311 with at least one through channel 1312, shown as two $1312_1$, $1312_2$, one of which $1312_2$ is offset from a centerline of the device guide. The device guide 1311 can be coupled to the trajectory frame 200. Rotating the device guide 1311 relative to the platform 132 can position the lumen/channel $1312_2$ at different circumferential locations.

Figure 7C:
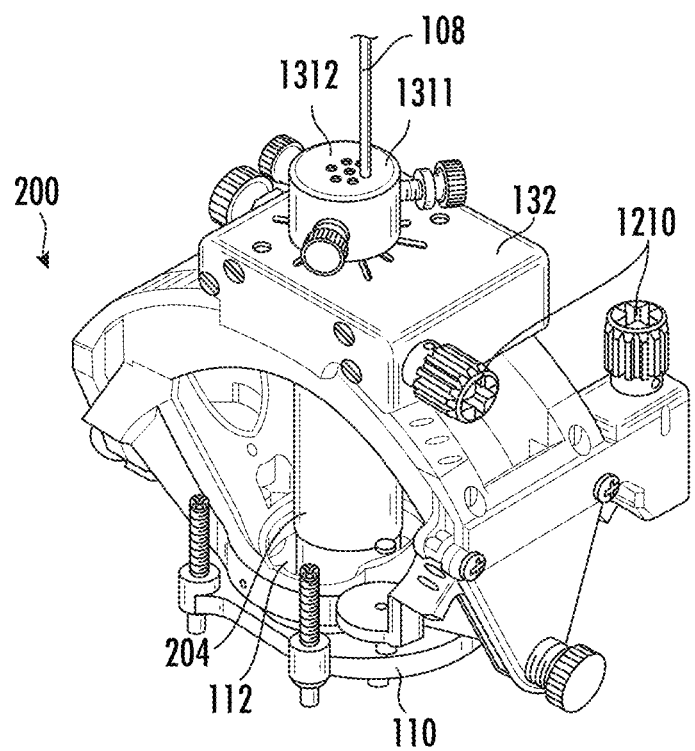
FIGS. 7C-7D are side perspective views of the example trajectory guide assembly shown in FIGS. 7A and 7B but with a different trajectory guide coupler and with a thermal treatment tool held therein according to embodiments of the present invention.
Figure 7D:
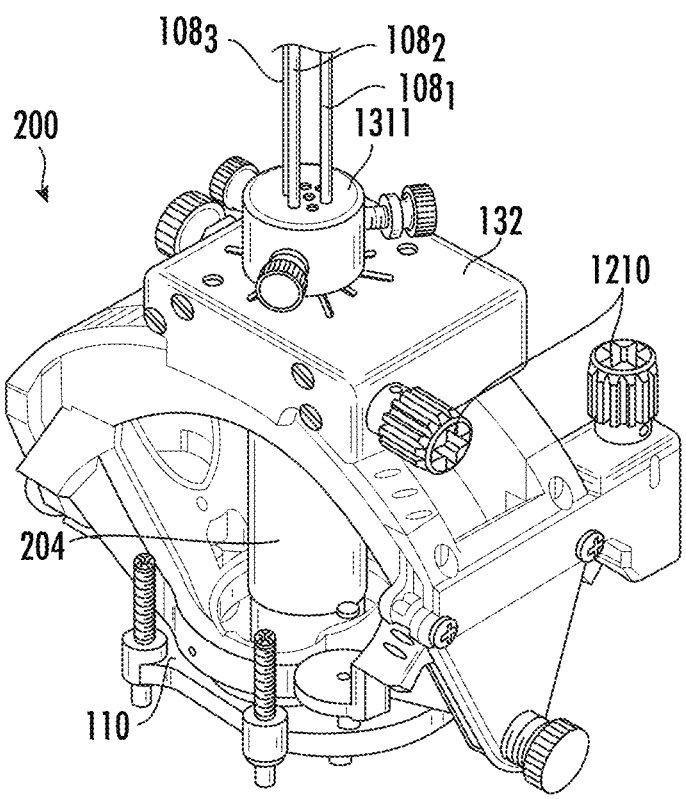

FIGS. 7C and 7D illustrate that a multi-lumen guide 1311 with an array of a plurality of spaced apart open through lumens/channels 1312 can be coupled to the trajectory frame 200.

The device guides 1311 can be used to place/insert the medical devices 108 through the trajectory guide 200 to provide the thermal treatment into the patient to the target site along a defined and controlled trajectory path (Pt, FIGS. 6C, 6D). In some embodiments, a plurality of medical devices $108_1$, $108_2$, $108_3$ can be concurrently inserted through the trajectory frame 200 and into a patient/subject (FIG. 11E). For more details of example multiple, double and single lumen device guides and trajectory guide assemblies, see, U.S. Pat. No. 10,905,498, the content of which is hereby incorporated by reference as if recited in full herein.

Figure 8:
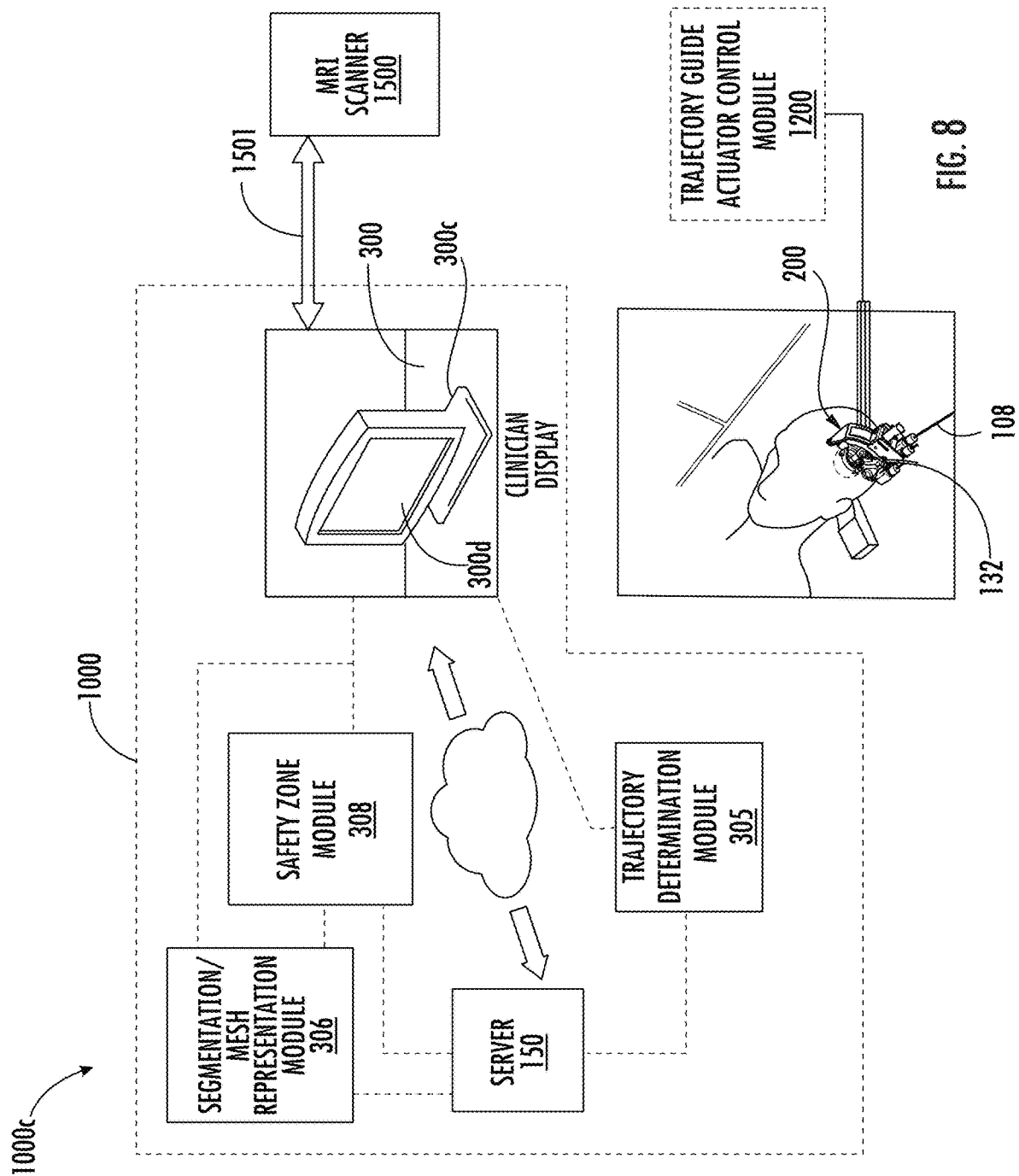
FIG. 8 is a schematic illustration of an image-guided surgical system according to some embodiments of the present invention.

FIG. 8 illustrates an image-guided surgical system 1000. The surgical system 1000 comprises a computer system 1000c and can comprise or communicate with a clinician workstation 300 and at least one display 300d. The computer system 1000c can comprise at least one data processing circuit 300c.

The surgical system 1000 can include a trajectory determination module 305. The workstation 300 can communicate with a scanner 1500, such as an MRI and/or CT scanner via an interface 1501 that may be used to allow communication between the workstation 300 and the scanner 1500. The interface 1501 and/or circuit 300c may comprise hardware, software or a combination of same. The interface 1501 and/or circuit 300c may reside partially or totally in the scanner 1500, partially or totally in the workstation 300, or partially or totally in a discrete device(s) therebetween.

The workstation 300 and/or circuit 300c can passively or actively communicate with the scanner 1500. The system 1000 can also be configured to use functional patient data (e.g., fiber tracks, fMRI and the like) to help plan or refine a target surgical site. See, e.g., U.S. Pat. No. 8,315,689 for additional information on example workflows and surgical systems, the contents of which are hereby incorporated by reference as if recited in full herein.

Still referring to FIG. 8, the surgical system 1000 can comprise a server 150 as part of the computer system 1000c that can provide and/or be in communication with one or more modules such as, a trajectory determination module 305, a brain segmentation and/or mesh representation module 306, a safety zone module 308, and a trajectory guide actuator control module 1200. The workstation 300 can communicate with the server 150 via a computer network, such as one or more of local area networks (LAN), wide area networks (WAN) and can include a private intranet and/or the public internet (also known as the World Wide Web or "the web" or "the internet"). The server 150 can include and/or be in communication with one or more of the modules 306, 308, 305, 1200 using appropriate firewalls for HIPAA (Health Insurance Portability Accountability Act) or other regulatory compliance.

The computer system 1000c and/or server 150 can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser) and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers.

The image-guided systems 1000 can be configured to carry out diagnostic and interventional procedures such as to guide and/or place interventional devices to any desired internal region of the body or object but may be particularly suitable for neurosurgeries. The object can be any object and may be particularly suitable for animal and/or human subjects. For example, the system can be used for gene and/or stem-cell based therapy delivery or other neural therapy delivery and allow user-defined custom targets in the brain or to other locations. In addition, embodiments of the systems can be used to thermally treat tissue (e.g., ablate, provide hyperthermia, provide hypothermia and/or provide combinations of same) in the brain or other locations and/or place electrode stimulation leads. In some embodiments, it is contemplated that the systems can be configured to treat AFIB in cardiac tissue, and/or to deliver stem cells or other cardio-rebuilding cells or products into cardiac tissue, such as a heart wall, via a minimally invasive MRI guided procedure while the heart is beating (i.e., not requiring a non-beating heart with the patient on a heart-lung machine). In some embodiments, the systems can be used to facilitate cell lysing to stimulate the immune system or other functional body systems.

Examples of known treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

The trajectory guide actuator control module 1200 can be used to automatically move actuators 1210 (FIGS. 7A-7D) of the trajectory guide 200 or provide movement directions for a user to manually move the actuators 1210 desired amounts to provide a selected candidate trajectory identified by the deformable brain model module 306 and/or trajectory determination module 306. The trajectory guide actuator control module 1200 can comprise MRI-compatible stepper motors that reside in a housing in an MRI scanner room, optionally coupled to the patient bed, so as to be able to move in and out of the bore of the magnet while coupled to the bed. See, e.g., U.S. Provisional Patent Application Ser. No. 62/988,609, filed Mar. 12, 2020, and U.S. patent application Ser. No. 17/185,060, the contents of which are hereby incorporated by reference as if recited in full herein.

To be clear, embodiments of the invention can be provided as a separate data processing system and/or module(s) or combined data processing systems and/or modules. The data processing system can be compatible with MRI and/or CT systems.

The MRI scanner 1500 can include a console that has a "launch" application or portal for allowing communication to the circuit 300c of the workstation 300. The scanner console can acquire volumetric image data of a respective patient, such as, for example, $T_1$-weighted (post-contrast scan) data or other image data (e.g., high resolution image data for a specific volume) of a patient's head and/or brain (or other target anatomy).

In some embodiments, the console can push DICOM images or other suitable image data to the workstation 300 and/or circuit 300c. The workstation 300 and/or circuit 300c can be configured to passively wait for data to be sent from the MR scanner 1500 and the circuit 300c/workstation 300 does not query the scanner or initiate a communication to the scanner. In other embodiments, a dynamic or active communication protocol between the circuit 300c/workstation 300 and the scanner 1500 may be used to acquire image data and initiate or request particular scans and/or scan volumes. Also, in some embodiments, pre-DICOM, but reconstructed image data, can be sent to the circuit 300c/workstation 300 for processing or display. In other embodiments, pre-reconstruction image data (e.g., substantially "raw" image data) can be sent to the circuit 300c/workstation 300 for Fourier Transform and reconstruction.

Embodiments of the invention are particularly useful for neurosurgeries such as deep brain surgeries. An end user, such as a neurosurgeon, can prepare, review and finalize inputs using a defined workflow. Once the inputs are provided (and also typically prepared and reviewed by a user), a defined set of rules can automatically determine orientation of a directional medical device to confirm no twisting or deviation and that data can be presented to the user, typically via a display of a computer system such as a clinician workstation.

The system 1000 can be configured to register CT image data and MRI image data by initiating automatic fusion of scans and allow/prompt a user to visually review image fusion results. Fusion tools can be used to allow a user to manually correct each incorrect fusion result. Automatic registration of a digital brain atlas to an MRI scan, such as a T1W scan, can be initiated and a user can be allowed/prompted to visually review registration results.

For identifying the potential entry points, all safety zones/no-go regions in the brain (at least those within any proximity to entry sites and target treatment volumes) can be segmented or otherwise identified. The outer surface of the head can be virtually divided into defined sub-areas, optionally with maximal outer perimeter sides in a range of 0.1 mm-2 mm, such as about 1 mm square sub-areas. Entry can be defined by a grid applied to the head of a subject. See, co-pending U.S. Provisional Patent Application Ser. No. 63/018,215, filed Apr. 30, 2020, for a discussion of an automated trajectory planning system, the contents of which are hereby incorporated by reference as if recited in full herein.

Embodiments of the present invention may take the form of an entirely software embodiment or an embodiment combining software and hardware aspects, all generally referred to herein as a "circuit" or "module." Furthermore, the present invention may take the form of a computer program product on a (non-transient) computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of data processing systems, method steps or actions, modules or circuits (or portions thereof) discussed herein may be written in a high-level programming language, such as Python, Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. As noted above, the functionality of any or all of the program modules may also be implemented using discrete hardware components, one or more application specific integrated circuits (ASICs), or a programmed digital signal processor or microcontroller. The program code may execute entirely on one (e.g., a workstation) computer, partly on one computer, as a stand-alone software package, partly on the workstation's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

The present invention is described in part with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing some or all of the functions/acts specified in the flowchart and/or block diagram block or blocks.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order or two or more blocks may be combined, depending upon the functionality.

Although not shown, in some embodiments, one or more of the directional medical devices 10 can be configured with one or more lumens and exit ports that deliver desired cellular, biological, and/or drug therapeutics to the target area, such as the brain. The tools may also incorporate transseptal needles, biopsy and/or injection needles as well as ablation devices. The lumens, where used, may receive extendable needles that may exit the probe from the distal end or from the sides, proximal, distal, or even, through the electrodes to precisely deliver cellular/biological therapeutics to the desired anatomy target. This delivery configuration may be a potential way to treat patients, where the cellular/biological therapeutics can be delivered into the desired anatomy to modify their cellular function. The cells (e.g., stem cells) may improve function. MRI can typically be effectively used to monitor the efficacy and/or delivery of the therapy.

Figure 9:
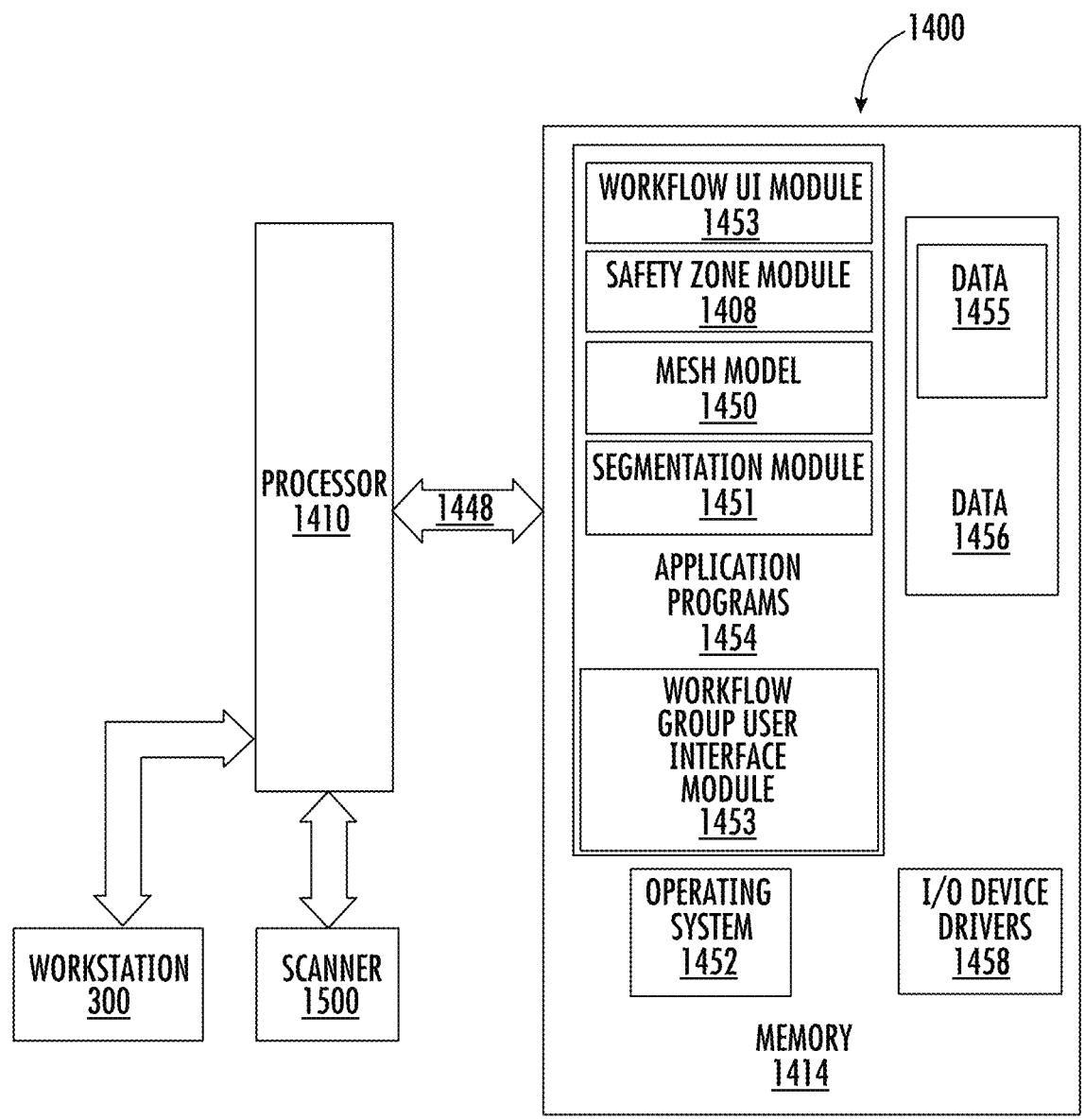
FIG. 9 is a schematic illustration of an example data processing system according to some embodiments of the present invention.

FIG. 9 is a schematic illustration of a data processing system 1400 that can be used with or define part of the image guided surgical system 1000. The data processing system may be incorporated in one or more digital signal processors in any suitable device or devices. As shown in FIG. 9, the processor 1410 can communicate with or be onboard the workstation 300 and/or can communicate with a scanner 1500 and with memory 1414 via an address/data bus 1448. The processor 1410 can be any commercially available or custom microprocessor. The memory 1414 is representative of the overall hierarchy of memory devices containing the software and data used to implement the functionality of the data processing system. The memory 1414 can include, but is not limited to, the following types of devices: cache, ROM, PROM, EPROM, EEPROM, flash memory, SRAM, and DRAM.

As shown in FIG. 9, the memory 1414 may include several categories of software and data used in the data processing system: the operating system 1452; the application programs 1454; the input/output (I/O) device drivers 1458; and data 1456. FIG. 9 also illustrates the application programs 1454 can include a (surface conformable and/or deformable) mesh model of module 1450, a segmentation module 1451, a safety zone module 1408, and a workflow User Interface module 1453 (that facilitates user actions and provides user review of orientation and/or intrabody trajectories for example).

As will be appreciated by those of skill in the art, the operating systems 1452 may be any operating system suitable for use with a data processing system, such as OS/2, AIX, DOS, OS/390 or System390 from International Business Machines Corporation, Armonk, NY, Window versions from Microsoft Corporation, Redmond, WA, Unix or Linux or FreeBSD, Palm OS from Palm, Inc., Mac OS from Apple Computer, LabView, or proprietary operating systems. The I/O device drivers 1458 typically include software routines accessed through the operating system 1452 by the application programs 1454 to communicate with devices such as I/O data port(s), data storage 1456 and certain memory 1414 components. The application programs 1454 are illustrative of the programs that implement the various features of the data processing system and can include at least one application, which supports operations according to embodiments of the present invention. Finally, the data 1456 represents the static and dynamic data used by the application programs 1454, the operating system 1452, the I/O device drivers 1458, and other software programs that may reside in the memory 1414.

While the present invention is illustrated, for example, with reference to the Modules 1450, 1451, 1408 and 1453 being application programs in FIG. 9, as will be appreciated by those of skill in the art, other configurations may also be utilized while still benefiting from the teachings of the present invention. For example, the Modules 1450, 1451, 1408, 1453 may also be incorporated into the operating system 1452, the I/O device drivers 1458 or other such logical division of the data processing system. Thus, the present invention should not be construed as limited to the configuration of FIG. 9 which is intended to encompass any configuration capable of carrying out the operations described herein. Further, one or more of modules, i.e., Modules 1450, 1451, 1408, 1453 can communicate with or be incorporated totally or partially in other components, such as a workstation, a scanner 1500 such as an MRI scanner, an interface device. Typically, the workstation 300 will include the modules 1450, 1451, 1408, 1453 and the scanner can include a module that communicates with the workstation 300 and can push image data thereto.

The Modules 1450, 1451, 1408, 1453 can be configured to carry out the methods of FIG. 5. The Modules 1450, 1451 can correspond to module 306 in FIG. 8. The module 1408 can correspond to module 308 in FIG. 8.

The I/O data port can be used to transfer information between the data processing system 1400, the computer system 1000c, the circuit 300c or workstation 300, the scanner 1500, and another computer system or a network (e.g., the Internet) or to other devices controlled by or in communication with the processor. These components may be conventional components such as those used in many conventional data processing systems, which may be configured in accordance with the present invention to operate as described herein.

FIGS. 10A and 10B are example schematic illustrations of thermal map overlays 600 showing temperature variation of tissue color coded to thermal temperatures according to embodiments of the present invention. FIG. 10B illustrates an appended scale 600s that correlates color to temperature (shown as a first temperature range starting at 42 degrees C. for a blue color, a second temperature range at about 58 degrees C. for a green color and a third temperature range at about 74 degrees C. for a red color).

Figure 11A:
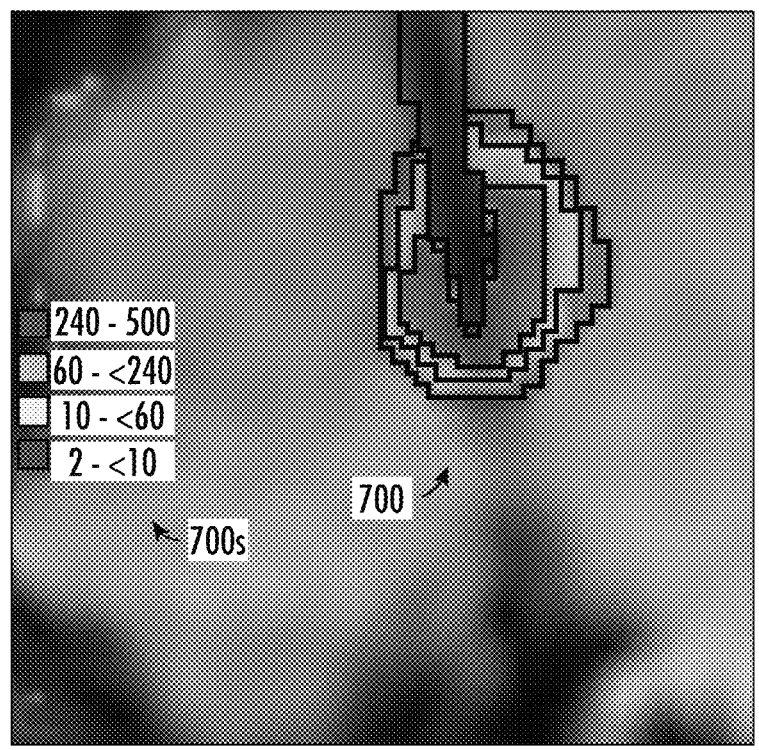
FIGS. 11A and 11B are a colorized (color-coded) estimate of thermal damage (cumulated thermal dose) of the tissue and corresponding temperatures shown in FIGS. 10A and 10B according to embodiments of the present invention.
Figure 11B:
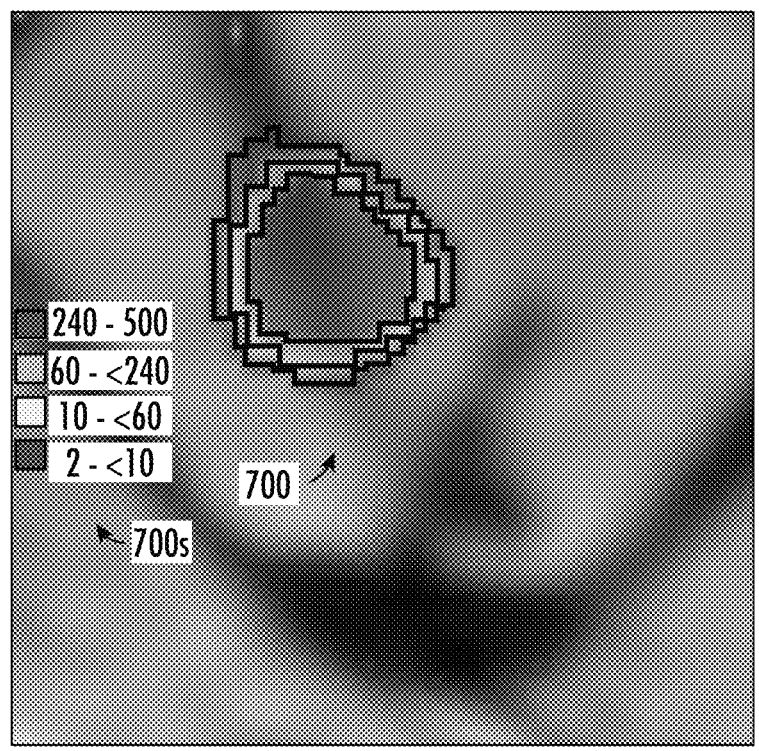

FIGS. 11A and 11B are a colorized (color-coded) overlays 700 estimate of thermal damage (cumulated thermal dose) of the tissue and corresponding temperatures shown in FIGS. 10A and 10B according to embodiments of the present invention. FIG. 11B illustrates an appended scale 700s that correlates color to thermal dose (CEM43, cumulative equivalent minutes at 43° C.).

As shown, a low/first dose range (2-<10) is shown in green, a second dose range (10-<60) is shown in yellow, a third dose range (60-<240) is shown in orange and a fourth dose range (the maximal dose range) of 240-500 is shown in red.

Figure 12A:
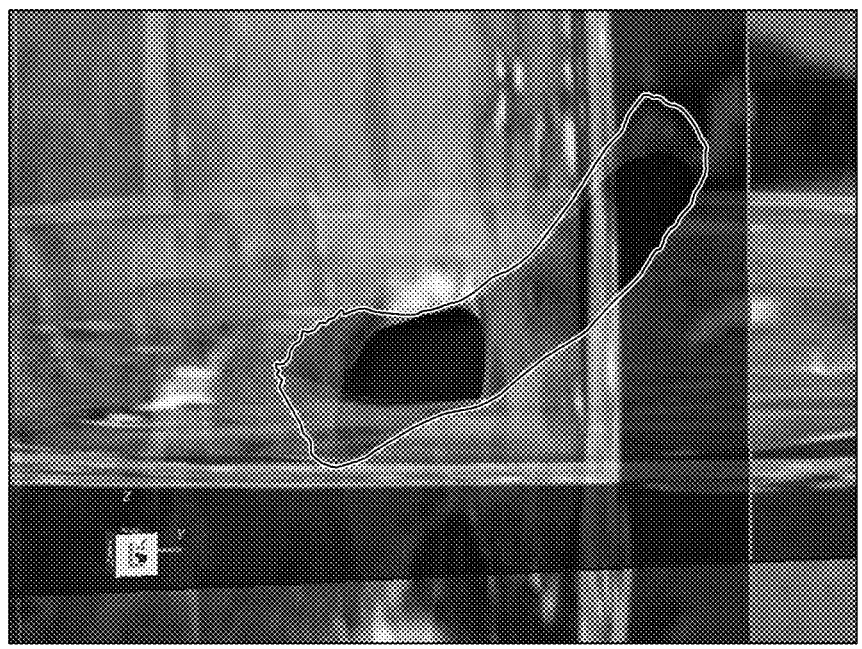
FIGS. 12A and 12B are example visualizations of a thermal treatment of a segmented hippocampus using a mesh representation.
Figure 12B:
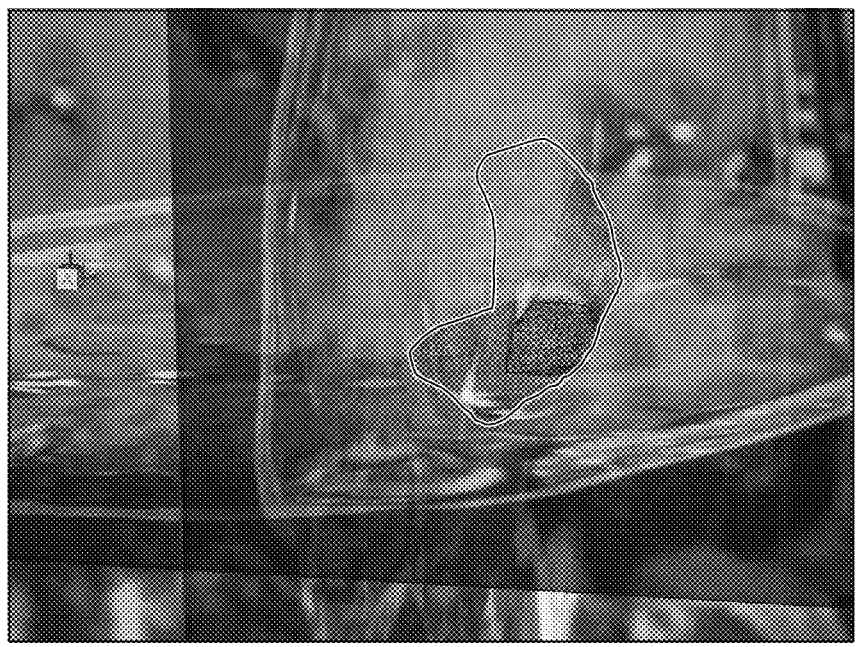

FIGS. 12A and 12B are example displays of visualizations illustrating a segmentation of the hippocampus. This is a common target for laser ablation, but the treated region can be any other brain structure or a lesion/tumor. In this example, the segmentation of the treated region shown in FIGS. 12A, 12B the hippocampus can be represented with a mesh surface of triangles. Instead of visualizing the mesh of the hippocampus in one color (blue in this case) as shown in FIG. 12A. The color of mesh vertices and/or or mesh faces, can be mapped to measured temperature(s). As a result, the temperature changes during an ablation can be visualized on the mesh surfaces. In FIG. 12A, the visualization captures only the temperature inside the region in the solid blue color.

Each mesh triangle (mesh face) has an inner and an outer surface/side. The visualization shows the outer side, or the part of the triangle facing outward rather than the interior/opposite side of the face).

Generally, as discussed above, color mapping assumes the same color for the entire mesh representation of a structure as shown in FIG. 12A. Texture mapping can assign different colors to mesh vertices and/or mesh element faces. The faces in this example case are shown as triangles but they can be any linear element (quads, hexagons, etc.) as also discussed above. The corners of each face are the mesh vertices as discussed with respect to FIG. 4. In this example, each triangle has three vertices, which are three points in 3-D space. Texture mapping can assign different colors to vertices 10v and faces 10f, and visualizations can provide measured temperature on the outer surface of the mesh elements. For example, the temperature can change from green (normal temperature) to red (ablated tissue) for different triangles on the mesh representing the treated region. That may be important because safety limits can be assigned to more discrete elements, such as mesh vertices or faces.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the dis- That which is claimed is:

1. An image-guided surgical system, comprising:
a workstation comprising a display;
a computer system in communication with or at least partially onboard the workstation, wherein the computer system is configured to:
provide visualizations of pre-operative high-resolution Magnetic Resonance Imaging (MRI) images of a brain of a patient to the display, wherein the visualizations are segmented to show patient-specific brain structures with corresponding three-dimensional mesh representations, each mesh representation having surface conformable mesh elements that cover a respective patient-specific brain structure including a first mesh representation for a first patient-specific brain structure associated with a target thermal treatment region and a second mesh representation for a second patient-specific brain structure outside the target thermal treatment region;
define at least one safety zone using one or more of the mesh elements of the second mesh representation;
monitor temperatures at each of a plurality of different mesh elements of the first mesh representation during an in vivo thermal treatment of the target thermal treatment region using MRI images; and
provide three-dimensional visualizations during the in vivo thermal treatment to the display that map the temperatures to the first mesh representation and the second mesh representation, wherein the provided three-dimensional visualizations comprise visualizations that texture map to color code the temperatures of different mesh elements of the first mesh representation during the in vivo thermal treatment.

2. The image-guided surgical system of claim 1, wherein the at least one safety zone is defined, at least in part, using vertex coordinates in MRI image space of at least one of the mesh elements of the second mesh representation and a distance of the at least one of the mesh elements to a trajectory line of a thermal treatment device providing the in vivo thermal treatment or distances from both the first mesh representation and the trajectory line to the at least one of the mesh elements of the second mesh representation.

3. The image-guided surgical system of claim 1, wherein the at least one safety zone is defined, at least in part, based on a location of at least one of the mesh elements of the second mesh representation or a vertex location of the at least one of the mesh elements of the second mesh representation corresponding to a mesh element that is closest to the first mesh representation or that is closest to a trajectory line of a thermal treatment device providing the in vivo thermal treatment.

4. The image-guided surgical system of claim 1, wherein the at least one safety zone is defined, at least in part, using a distance of a line that is normal to a surface defined by one or more of the mesh elements.

5. The image-guided surgical system of claim 1, wherein the mesh elements are triangular mesh elements, each having three vertices.

6. The image-guided surgical system of claim 5, wherein the mesh elements share one or more vertices.

7. The image-guided surgical system of claim 1, wherein the first and second mesh representations each comprise a contiguous configuration of a plurality of mesh elements, each mesh element comprising at least a first vertex, a second vertex and a third vertex surrounding a mesh face, and wherein the computer system is configured to map the monitored temperatures to different mesh faces of the mesh elements.

8. The image-guided surgical system of claim 1, wherein the computer system is further configured to:
obtain high-resolution MRI images during the in vivo thermal treatment;
register the pre-operative high-resolution MRI images to the obtained high-resolution MRI images; and
detect intensity changes in regions of interest in the first mesh representation and the second mesh representation relative to baseline values in the pre-operative high-resolution MRI images in near real-time during the in vivo thermal treatment.

9. An image-guided surgical system, comprising:
a workstation comprising a display;
a computer system in communication with or at least partially onboard the workstation, wherein the computer system is configured to:
provide visualizations of pre-operative high-resolution Magnetic Resonance Imaging (MRI) images of a brain of a patient to the display, wherein the visualizations are segmented to show patient-specific brain structures with corresponding three-dimensional mesh representations, each mesh representation having surface conformable mesh elements that cover a respective patient-specific brain structure including a first mesh representation for a first patient-specific brain structure associated with a target thermal treatment region and a second mesh representation for a second patient-specific brain structure outside the target thermal treatment region;
define at least one safety zone using one or more of the mesh elements of the second mesh representation;
monitor temperatures during an in vivo thermal treatment of the target thermal treatment region using MRI images and the first and second mesh representations; and
provide three-dimensional visualizations during the in vivo thermal treatment to the display that map the temperatures to the first mesh representation and the second mesh representation,
wherein a defined temperature is encoded to vertices of different mesh elements of the second mesh representation.

10. The image-guided surgical system of claim 1, wherein the computer system is further configured to evaluate one or more of a center of mass, a principal axis and a mesh curvature of the mesh elements whereby one or more of the center of mass, principal axis, mesh curvature are used to define trajectories for defining coverage for the in vivo thermal treatment.

11. The image-guided surgical system of claim 1, in combination with an MRI scanner, wherein the workstation is in communication with the MRI scanner, wherein the workstation comprises a DICOM interface that receives images from the MRI scanner to provide image data during the in vivo thermal treatment.

12. The image-guided surgical system of claim 1, wherein the in vivo thermal treatment is an ablation, and wherein the provided three-dimensional visualizations during the in vivo thermal treatment show successively acquired images of volumes of ablated tissue and functional integrity and connectivity of ablated regions during the in vivo thermal treatment.

13. The image-guided surgical system of claim 1, wherein the in vivo thermal treatment is a laser interstitial thermal therapy (LITT).

14. The image-guided surgical system of claim 1, wherein the pre-operative high-resolution MRI images comprise T1-weighted images.

15. The image-guided surgical system of claim 1, wherein the provided visualizations further comprise visualizations that color code a calculated thermal dose received at the target thermal treatment region based, at least in part, on the monitored temperatures of the mesh elements of the first mesh representation.

16. An image-guided surgical system, comprising:
a workstation comprising a display;
a computer system in communication with or at least partially onboard the workstation, wherein the computer system is configured to:
provide visualizations of pre-operative high-resolution Magnetic Resonance Imaging (MRI) images of a brain of a patient to the display, wherein the visualizations are segmented to show patient-specific brain structures with corresponding three-dimensional mesh representations, each mesh representation having surface conformable mesh elements that cover a respective patient-specific brain structure including a first mesh representation for a first patient-specific brain structure associated with a target thermal treatment region and a second mesh representation for a second patient-specific brain structure outside the target thermal treatment region;
define at least one safety zone using one or more of the mesh elements of the second mesh representation;
monitor temperatures during an in vivo thermal treatment of the target thermal treatment region using MRI images and the first and second mesh representations; and
provide three-dimensional visualizations during the in vivo thermal treatment to the display that map the temperatures to the first mesh representation and the second mesh representation,
wherein a defined temperature(s) is encoded to the mesh elements of at least the first mesh representation.

17. The image-guided surgical system of claim 9, wherein the defined temperature is a minimum treatment temperature or a maximum treatment temperature at the mesh elements of the second mesh representation.

18. A method of monitoring an in vivo thermal treatment of a brain of a patient, comprising:
providing pre-operative high-resolution MRI images of the brain of the patient segmented with three-dimensional surface conformable mesh representations comprising mesh elements to show respective segmented patient-specific brain structures;
defining a target treatment region comprising a first one of the three-dimensional surface conformable mesh representations;
defining a safety zone comprising a second one of the three-dimensional surface conformable mesh representations that is outside the target treatment region;
obtaining high-resolution MRI images during the in vivo thermal treatment; and
providing visualizations to a display that show at least one of thermally treated volumes or sub-volumes within the first and second three-dimensional surface conformable mesh representations that are texture mapped to at least one of mesh vertices or faces of the mesh elements during the in vivo thermal treatment, wherein each of the mesh elements comprise at least a first vertex, a second vertex, and a third vertex surrounding a mesh face, and wherein the method comprises mapping measured temperatures, by color, to different mesh faces of the mesh elements whereby different mesh faces can indicate different temperatures based on a currently monitored temperature thereat.

19. The method of claim 18, further comprising calculating a distance of at least one of the mesh elements of the second mesh representation from the first mesh representation or a distance of the at least one of the mesh elements of the second mesh representation from a trajectory line of a laser providing the in vivo thermal treatment or distances from both the first mesh representation and the trajectory line to the at least one of the mesh elements of the second mesh representation.

20. The method of claim 18, further comprising determining temperatures at different mesh element locations of the first and second mesh representations at different successive times during the in vivo thermal treatment for the visualizations.

21. The method of claim 18, wherein the thermal treatment is an ablation, and wherein the provided visualizations show increased volumes of ablated tissue over time as the thermally treated volumes or sub-volumes and functional integrity and connectivity of ablated regions during the in vivo thermal treatment.

22. The method of claim 18, wherein the in vivo thermal treatment is a laser interstitial thermal therapy (LITT).

23. The method of claim 18, wherein the safety zone is defined, at least in part, using vertex coordinates in MR imaging space of at least one of the mesh elements of the second mesh representation and a distance of the at least one of the mesh elements from a trajectory line of a thermal treatment device providing the in vivo thermal treatment or distances from both the first mesh representation and the trajectory line to the at least one of the mesh elements of the second mesh representation.

24. The method of claim 18, wherein the safety zone is defined, at least in part, based on a location of at least one of the mesh elements of the second mesh representation or a vertex location of the at least one of the mesh elements of the second mesh representation corresponding to a mesh element that is closest to the first mesh representation or that is closest to a trajectory line of a thermal treatment device providing the in vivo thermal treatment.

25. The method of claim 18, wherein the safety zone is defined, at least in part, using a distance of a virtual line that is normal to a surface defined by one or more of the mesh elements.

26. The method of claim 18, wherein the mesh elements are triangular mesh elements, each having three vertices.

* * * * *

UNITED STATES PATENT AND TRADEMARK OFFICE
CERTIFICATE OF CORRECTION

PATENT NO. : 12,102,489 B2
APPLICATION NO. : 17/725077
DATED : October 1, 2024
INVENTOR(S) : Zagorchev et al.

Page 1 of 1

It is certified that error appears in the above-identified patent and that said Letters Patent is hereby corrected as shown below:

In the Specification

Column 11, Line 48: Please correct "101" to read --10*i*--

Column 18, Line 13: Please correct "$T_1$-weighted" to read --T1-weighted--

In the Claims

Column 25, Line 41, Claim 16: Please correct "temperature(s)" to read --temperature--

Signed and Sealed this
Tenth Day of December, 2024

Katherine Kelly Vidal
*Director of the United States Patent and Trademark Office*